(12) United States Patent
Yasuzawa et al.

(10) Patent No.: US 8,364,233 B2
(45) Date of Patent: Jan. 29, 2013

(54) BIODEVICE AND CONTACT PART STRUCTURE OF BIODEVICE

(75) Inventors: Mikito Yasuzawa, Tokushima (JP); Shinya Furukawa, Itano-gun (JP)

(73) Assignee: The University of Tokushima, Tokushima (JP)

( * ) Notice: Subject to any disclaimer, the term of this patent is extended or adjusted under 35 U.S.C. 154(b) by 1003 days.

(21) Appl. No.: 12/278,829

(22) PCT Filed: Feb. 8, 2007

(86) PCT No.: PCT/JP2007/052214
§ 371 (c)(1),
(2), (4) Date: Nov. 7, 2008

(87) PCT Pub. No.: WO2007/091633
PCT Pub. Date: Aug. 16, 2007

(65) Prior Publication Data
US 2009/0069654 A1    Mar. 12, 2009

(51) Int. Cl.
*A61B 5/04* (2006.01)
*C12M 1/34* (2006.01)
(52) U.S. Cl. ........ 600/372; 600/325; 600/347; 600/365; 600/373; 422/402; 422/405; 422/410; 422/426; 435/287.1; 435/287.3; 436/14; 436/148

(58) Field of Classification Search .................. 422/402, 422/405, 408, 410, 419, 426, 520, 524, 554; 435/14, 25, 287.1, 287.3, 287.9; 436/518, 436/14, 52, 54, 148; 600/325, 347, 365, 600/372, 373
See application file for complete search history.

(56) References Cited

U.S. PATENT DOCUMENTS
6,051,392 A    4/2000    Ikeda et al.

FOREIGN PATENT DOCUMENTS

| EP | 0 964 060 | * 12/1999 |
|----|-----------|-----------|
| JP | 58-86449 | 5/1983 |
| JP | 07-39931 | 7/1995 |
| JP | 07-213926 | 8/1995 |
| JP | 11-352092 | 12/1999 |
| JP | 2000-254112 | 9/2000 |
| JP | 2003-038464 | 2/2003 |

OTHER PUBLICATIONS

WO patent application No. PCT/JP2007/052214, International Search Report mailed May 22, 2007.

* cited by examiner

*Primary Examiner* — Gail R Gabel
(74) *Attorney, Agent, or Firm* — Weaver Austin Villeneuve & Sampson LLP

(57) ABSTRACT

A biodevice is in an elongated form and has a conductive layer and an insulating layer stacked on a side surface of a shaft member at the center. A cylindrical hollow section is formed through the device, being connected to the exterior at a front end and extending from this front end axially. An electrode section is formed on an inner surface. A sensing substance such as enzyme may be placed at the electrode section to detect a current value corresponding to the concentration or quantity of an object under test placed between a counter electrode and the biodevice.

10 Claims, 19 Drawing Sheets

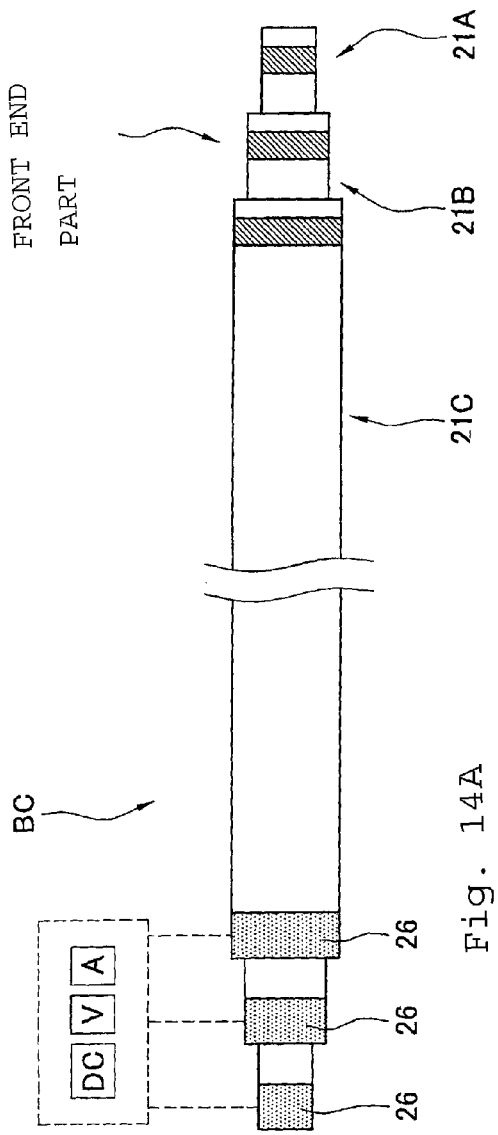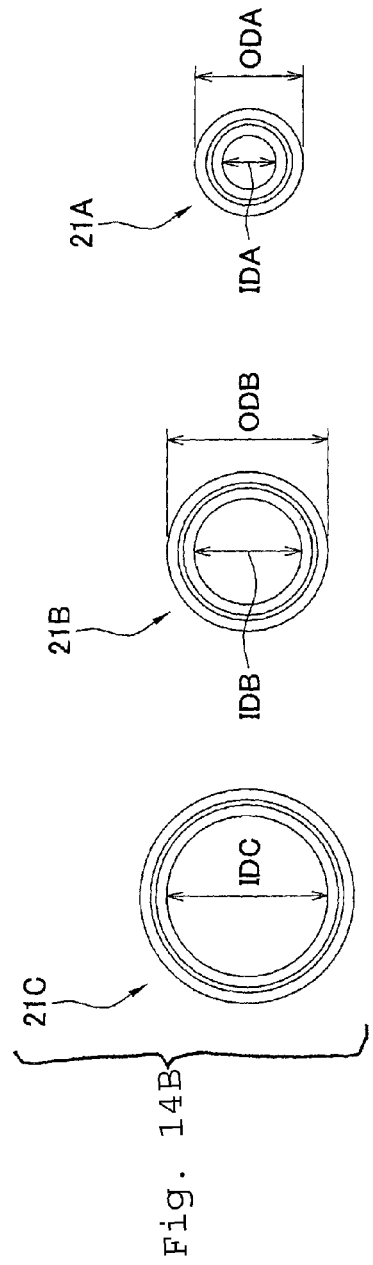
Fig. 14A
Fig. 14B

BIODEVICE AND CONTACT PART STRUCTURE OF BIODEVICE

This application is a continuation of International Application No. PCT/JP2007/052214, filed Feb. 8, 2007 which claims priority on Japanese Patent Applications 2006-032275 filed Feb. 9, 2006 and 2006-041358 files Feb. 17, 2006.

BACKGROUND OF THE INVENTION

This invention relates to biodevices and contact part structures of biodevices. A so-called enzyme sensor having a specified kind of enzyme attached to the surface of an electrode is used for measuring the concentration of sugar, amino acids, etc. in an organism. Such an sensor is used for making use of the characteristic of the enzyme attached to the electrode for singularly oxidizing or reducing sugar and amino acids to generate molecules and ions, and the concentration of sugar, amino acids, etc. can be measured by detecting the quantity of the generated molecules and ions as the value of the current that flows in the electrode. If the kind of the enzyme attached to the surface of the electrode is changed, furthermore, the type of the substance to be measured can be changed.

This invention relates to biosensors that are usable for measuring the concentration, etc. of such substances in an organism, biodevices that are usable for such biosensors, and contact part structures of such biodevices.

Glucose sensors for measuring the glucose concentration in an organism are being developed as an example of conventionally used enzyme sensor (as disclosed in Japanese Patent Publication Tokkai 5-60722; and W. Kenneth Ward, Lawrence B, Jansen, Ellen Anderson, Gerard Reach, Jean-Claude Klein, and George S. Wilson, "A new amperometric glucose microsensor: in vitro and short-term in vitro evaluation", Biosensors & Bioelectronics 17, 2002, p. 181-189).

Since these devices have an electrode exposed to the surface and enzyme, etc. are attached to this electrode, one cannot deny the possibility of the enzyme becoming displaced or the sensing parts becoming damaged as the device is inserted into an organism.

As an example of device having an electrode that is not exposed externally, a probe having an indentation formed at the end is being developed (Japanese Patent Publication Tokkai 11-347019). This probe is for examining blood or body fluid taken from an organism and is structured such that an electrode and a reagent to be used for detection of the object under test are disposed inside the indentation. It is documented that the quantity of the blood to be examined can be maintained constant by the volume of the indentation as the examination is carried out with a body fluid contained inside the indentation of the probe.

In recent years, biosensors to be used by penetrating or placing inside an organism are being required, and such biosensors are required to be able to carry out measurements accurately for a long period of time. In order to improve the sensitivity of a biosensor, it is necessary to make the area of its electrode (and in particular its working electrode) large and it is necessary to be able to hold a large amount of enzyme for a long time of use.

Since the probe according to aforementioned Japanese Patent Publication Tokkai 11-347019 uses the end of a working electrode lead at the center of the probe as its working electrode, it is necessary to make the working electrode lead thick in order to make the area of the electrode large. Since the probe itself will become thick if the working electrode lead is made thick, however, the damage to the organism also becomes large when it is used to penetrate it or place inside.

Moreover, since this probe has its hollow section formed in a semispherical shape, the radius of this hollow section must be increased if it is desired to hold a large quantity of enzyme. In such a situation, the probe itself must also be made thick.

Accordingly, this probe can be used for detecting an object under test inside a target object taken or separated from an organism but is not suitable for a device for directly detecting and measuring inside an organism without collecting any object under test inside the organism.

Although it would be very useful if it were possible to combine a biosensor in a treatment using an endoscope or a catheter used by inserting into an organism, such a biosensor allowing to be effectively combined to an endoscope or a catheter has not been developed and its development is being wished for.

SUMMARY OF THE INVENTION

It is therefore an object of this invention, in view of the situation as described above, to provide a biosensor capable of directly detecting and measuring an object under test inside an organism by inserting or placing inside the organism and further of preventing the region being sensed from being damaged while keeping the region being sensed very small, as well as a biodevice usable for such a biosensor and a contact part structure of the biodevice.

It is another object of this invention to provide such a biosensor capable of inspecting a plurality of substances simultaneously and applicable to a tubular or linear-shaped medical equipment such as catheters, optical sensors, light sources, heat sources, excitation electrodes and endoscopes, as well as biodevices applicable to a biosensor.

A biodevice according to a first aspect of this invention is characterized as being formed in an elongated form (herein also referred to as being "rod-shaped") and comprising a shaft member at a center position, the shaft member extending in an axial direction, and a conductive layer and an insulating layer which are stacked on a side surface of the shaft member in a direction transverse to the axial direction, wherein the biodevice has a cylindrical hollow section formed therethrough, being connected to the exterior at a front end and extending from the front end in the axial direction, the hollow section having an electrode section on an inner surface.

A biodevice according to a second aspect of this invention is characterized as being one according to the first aspect of this invention wherein the electrode section is formed along the inner surface of the hollow section so as to have an approximately cylindrical surface.

A biodevice according to a third aspect of this invention is characterized as being one according to the second aspect of this invention wherein the electrode section is formed by a part of the conductive layer.

A biodevice according to a fourth aspect of this invention is characterized as being one according to the first aspect of this invention wherein the hollow section is formed such that a front end of the shaft member is disposed at an inner bottom part of the hollow section.

A biodevice according to a fifth aspect of this invention is characterized as being one according to the first aspect of this invention adapted for use with a front end part disposed inside an organism, having a shaft diameter of 500 µm or less and the shaft diameter becoming smaller towards the front end part.

A biodevice according to a sixth aspect of this invention is characterized as being one according to the second aspect of this invention wherein the hollow section contains a member that varies volume or affinity by an external stimulus.

A contact part structure of a biodevice according to a seventh aspect of this invention is a structure of a contact part of a device adapted to be placed in an organism, a base of this device being connected to a base end, this contact part being adapted to contact the organism, wherein the contact part structure is provided with a shaft member at a center position of the contact part structure, the shaft member extending in an axial direction, and a conductive layer and an insulating layer which are stacked on a side surface of the shaft member in a direction transverse to the axial direction, and wherein the contact part structure has a cylindrical hollow section formed therethrough, being connected to the exterior at a front end and extending from the front end in the axial direction, the hollow section having an electrode section on an inner surface.

A contact part structure according to an eighth aspect of this invention is one according to the seventh aspect of this invention wherein the electrode section is formed along the inner surface of the hollow section so as to have an approximately cylindrical surface.

A contact part structure according to a ninth aspect of this invention is one according to the eighth aspect of this invention wherein the electrode section is formed by a part of the conductive layer.

A contact part structure according to tenth aspect of this invention is one according to the seventh aspect of this invention wherein the hollow section is formed such that a front end of the shaft member is disposed at an inner bottom part of the hollow section.

A contact part structure according to an eleventh aspect of this invention is one according to the seventh aspect of this invention adapted for use with a front end part disposed inside an organism, having a shaft diameter of 500 μm or less and the shaft diameter becoming smaller towards the front end part.

A contact part structure according to a twelfth aspect of this invention is one according to the seventh aspect of this invention wherein the hollow section contains a member that varies volume or affinity by an external stimulus.

According to the second aspect of the invention, the area of the electrode section can be increased by increasing the length of the electrode section in the axial direction of the rod-shaped device without increasing the sectional area of the rod-shaped device or the hollow section. Since the area for applying a voltage can thus be increased, it becomes possible to cause more current to flow. If it is used as a biosensor, this improves the sensitivity of the biosensor. If the area of the electrode can be increased, this means that more sensing substance can be contained near the electrode inside the hollow section and hence the sensor sensitivity can be improved while maintaining the response speed of the sensor.

According to the third aspect of the invention, the conductive layer can be utilized as a lead line and the rod-shaped device can be made thinner.

According to the fourth aspect of the invention, since the front end of the shaft member is disposed at an inner bottom part of the hollow section, the material inside the hollow section can be heated if the shaft member comprises a material having high thermal conductivity. If the shaft member comprises a material such as optical fibers, the material inside the hollow section can be irradiated with light.

According to the fifth aspect of the invention, the biodevice can be inserted or penetrated into an organism and also kept buried inside an organism. It is also possible to reduce the burden on the organism when it is placed therein. For example, the generation of pain can be controlled and the wound can be made smaller.

According to the sixth aspect of the invention, if a member that varies volume or affinity by an external stimulus is contained, it becomes possible to supply the material contained inside the hollow section near the front end of the rod-shaped device or collect material near the front end of the rod-shaped device.

According to the seventh aspect of the invention, if a counter electrode is set near the contact part and a voltage is applied between the counter electrode and the electrode section, a current can be made to flow through a material that exists between them. If a sensing substance such as enzyme is placed on the surface of the electrode section, a current value corresponding to the concentration and quantity of an object under test placed between the counter electrode and the contact part can be detected. Since the electrode is provided on the inner surface of the hollow section of the rod-shaped device, furthermore, the electrode section can be prevented from becoming damaged or dropping off even when the rod-shaped device is inserted into an organism. Moreover, if the hollow section is filled with the sensing substance, the area for sensing becomes the front end open region of the hollow section. If the front open region is made smaller, the contacting area between the sensing substance and the object under test becomes small and it becomes possible to inspect even over a small region. Since the quantity of the sensing substance becoming free and scattering away can be reduced, the useful lifetime of the sensor can be improved. If the length of the hollow section in the axial direction of the contact part is increased, furthermore, the volume of the hollow section can be increased independent of its sectional area and hence the amount of the sensing substance to be contained inside the hollow section can be increased and the sensing substance in an amount necessary for the detection can be kept inside the hollow section for a longer period of time and hence the useful lifetime of the sensor can be made longer. Since the force applied to the contact part can be supported by the shaft member, the contact part can be reliably prevented from becoming damaged by being bent and can be reliably inserted into an object of inspection such as an organism.

According to the eighth aspect of the invention, the area of the electrode section can be increased by increasing the length of the electrode section in the axial direction of the contact part without increasing the sectional area of the contact part or the hollow section. Since the area for applying a voltage can thus be increased, it becomes possible to cause more current to flow. If it is used as a biosensor, this improves the sensitivity of the biosensor. If the area of the electrode can be increased, this means that more sensing substance can be contained near the electrode inside the hollow section and hence the sensor sensitivity can be improved while maintaining the response speed of the sensor.

According to the ninth aspect of the invention, the conductive layer can be utilized as a lead line and the contact part can be made thinner.

According to the tenth aspect of the invention, since the front end of the shaft member is disposed at an inner bottom part of the hollow section, the material inside the hollow section can be heated if the shaft member comprises a material having high thermal conductivity. If the shaft member comprises a material such as optical fibers, the material inside the hollow section can be irradiated with light.

According to the eleventh aspect of the invention, the biodevice can be inserted or penetrated into an organism and also kept buried inside an organism. It is also possible to reduce the burden on the organism when it is placed therein. For example, the generation of pain can be controlled and the wound can be made smaller.

According to the twelfth aspect of the invention, if a member that varies volume or affinity by an external stimulus is contained, it becomes possible to supply the material contained inside the hollow section near the front end of the contact part or collect material near the front end of the contact part.

BRIEF DESCRIPTION OF THE DRAWINGS

FIGS. 14A and 14B, together referred to as FIG. 14, show a biosensor according to this invention, FIG. 14A being its schematic side view and FIG. 14B being its sectional views.

DETAILED DESCRIPTION OF THE INVENTION

Embodiments of the invention are explained next with reference to the drawings.

Figure 1A:
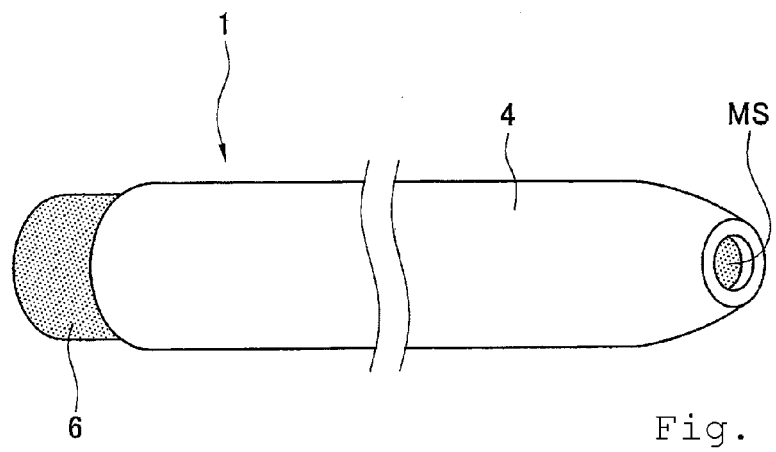
FIG. 1, consisting of FIGS. 1A, 1B and 1C, schematically shows a rod-shaped device which is one embodiment of the biodevice according to this invention, FIG. 1A being its schematic side view, FIG. 1B being a schematic enlarged view of its end and FIG. 1C being its sectional view taken along line 1C-1C of FIG. 1B.
Figure 1B:
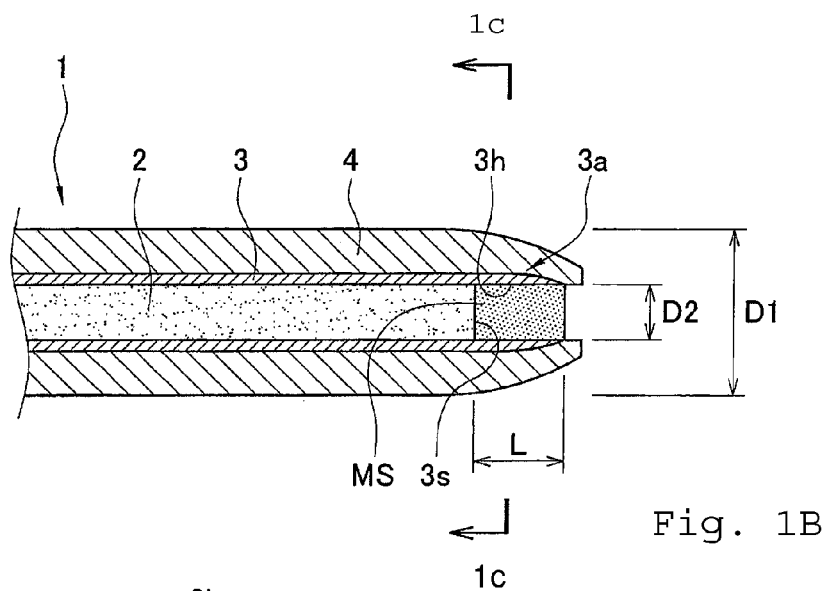
Figure 1C:
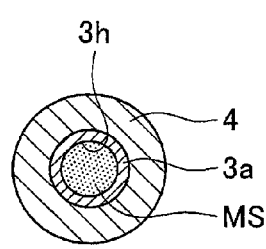

FIG. 1 is for schematically showing a rod-shaped device 1 which is one embodiment of the biodevice according to this invention, FIG. 1A being its schematic side view, FIG. 1B being a schematic enlarged view of its end and FIG. 1C being its sectional view taken long line IC-IC of FIG. 1B.

In the figures which are intended to make the structure of a biodevice and a biosensor easier to understand, the sizes and relative ratios of thickness and length of their components are not realistically represented. For the rod-shaped device 1 according to this invention shown in FIG. 1, if its outer diameter is about 0.3-500 μm, it is preferable that the outer diameter of its shaft member 2 be about 0.1-300 μm, the thickness of its conductive layer 3 be about 0.05-100 μm and the thickness of its insulating layer 4 be about 0.05-100 μm but the diameter of the shaft member 2 and the thicknesses of the conductive layer 3 and the insulating layer 4 are not limited to the ranges described above. The conductive layer 3 and the insulating layer 4 may be of the same thickness but if the conductive layer 3 is made thinner than the insulating layer 4, it is possible to control the outer diameter of the rod-shaped device 1 from becoming too large while reducing the possibility of the short-circuiting of the conductive layer 3 with other substances.

Next, the rod-shaped device 1, which is one embodiment of biodevice of this invention, is explained.

In FIG. 1, numeral 1 indicates a rod-shaped device as one embodiment of biodevice of this invention. This rod-shaped device 1 is a linear device, or an elongated member, extending in an axial direction (the left-right direction in FIG. 1).

Figure 4A:
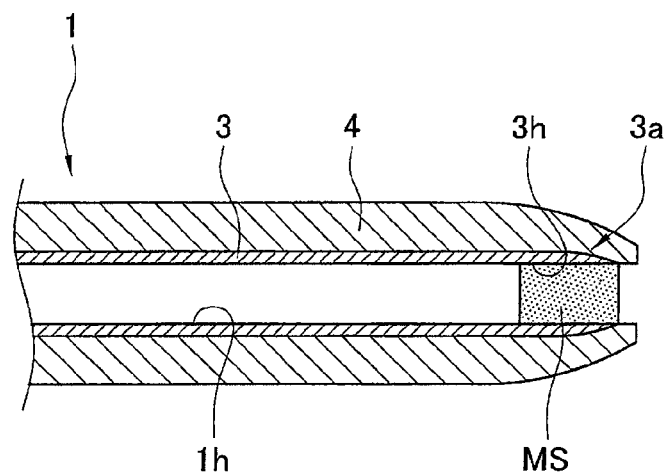
FIGS. 4A and 4B, together referred to as FIG. 4, are schematic enlarged sectional views of end parts of rod-shaped devices according to other embodiments.

Although the rod-shaped device 1 is shown as being provided at its center with a shaft member 2 extending in the axial direction, this shaft member 2 need not necessarily be provided. A throughhole 1h may be provided as shown in FIG. 4A in the axial direction of the rod-shaped device 1, instead of providing the shaft member 2.

Although FIG. 1 shows the rod-shaped device 1 as having a circular sectional shape, its sectional shape is not limited to be circular but may be a semi-circle, a square, a rectangle or a polygon such as a hexagon or an octagon.

A layer made of a conductive material (conductive layer 3) and another layer made of an insulating material (insulating layer 4) are alternately provided to the side surface of the shaft member 2 along a direction transverse to the axial direction of the shaft member 2 (axial direction of the rod-shaped device 1).

Figure 2A:
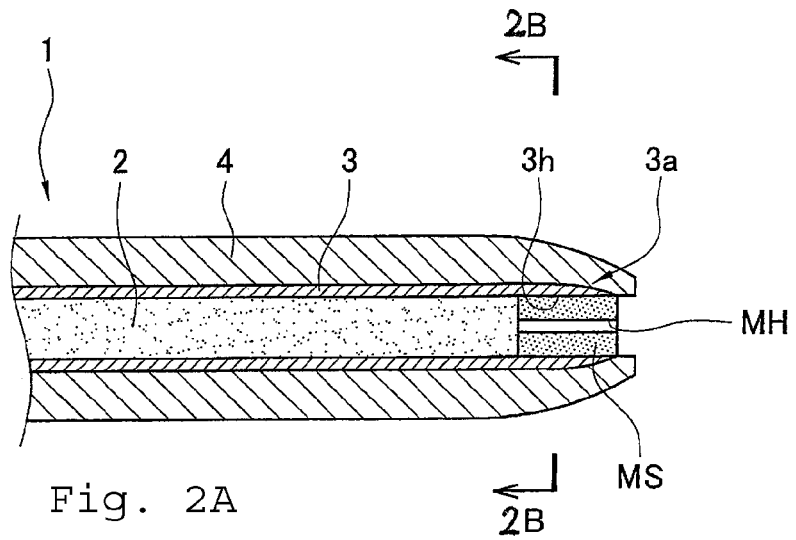
FIG. 2A is a schematic enlarged sectional view of an end part of a rod-shaped device according to another embodiment.
Figure 2B:
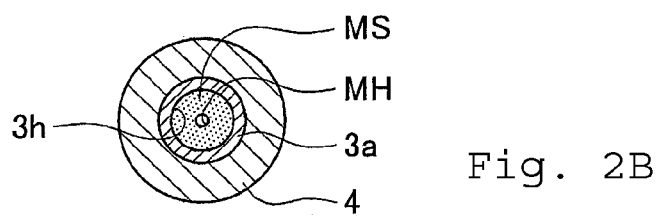
FIG. 2B is a sectional view take along line 2B-2B of FIG. 2A.
Figure 2C:
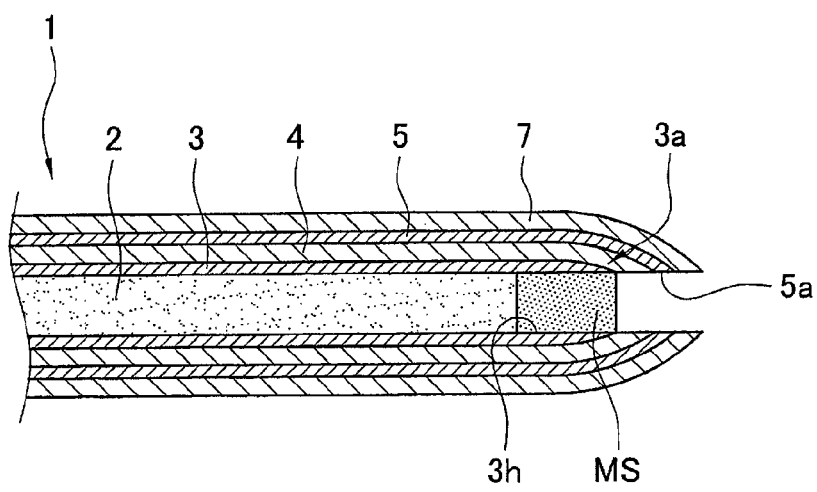
FIG. 2C is a schematic enlarged sectional view of an end part of a rod-shaped device according to still another embodiment.
Figure 3A:
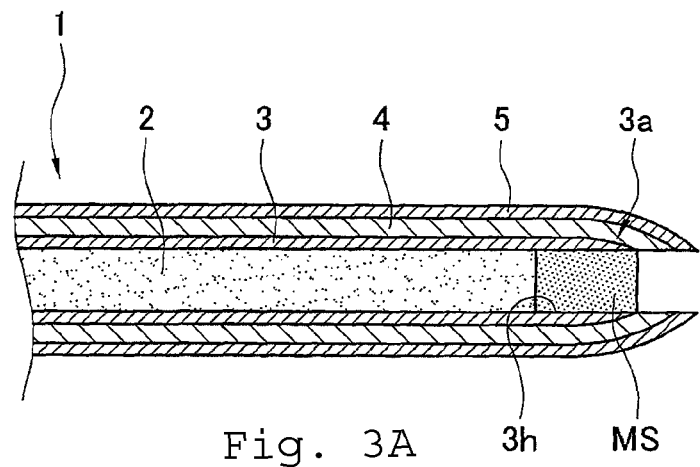
FIGS. 3A, 3B and 3C, together referred to as FIG. 3, are schematic enlarged sectional views of end parts of rod-shaped devices according to other embodiments.

Although FIG. 1 shows an example wherein there is one conductive layer and one insulating layer, pluralities of conductive and insulating layers may be provided as long as they are formed alternately, as shown in FIGS. 2C and 3A.

Although FIG. 1 shows an example wherein a conductive layer 3 is formed on the side surface of the shaft member 2, it goes without saying that it may be an insulating layer 4 that is formed on the side surface of the shaft member 2, an insulating layer 4 being formed on the surface of this conductive layer 3.

As shown in FIG. 1, a hollow section 3h is formed at an end (right-hand end in FIG. 1) of the rod-shaped device 1, indenting inward from the end surface. In other words, the hollow section 3h is formed so as to connect to the exterior at the end of the rod-shaped device 1. This hollow section 3h is formed in a cylindrical form extending along the axial direction of the rod-shaped device 1. Although this hollow section 3h is formed such that its inner diameter D2 is about 0.1-300 µm if the outer diameter D1 of the rod-like device is about 0.3-500 µm, there is no particular limitation placed on the ratio of the inner diameter D2 with respect to the outer diameter D1. The sectional area of the hollow section 3h in the axial direction need not be constant. The sectional area of the inner part may be made larger than that at the end of the rod-shaped device 1, as shown in FIG. 3C.

As for the sectional shape of the hollow section 3h, it is only required to be cylindrically formed and its sectional shape need not be circular but may be semicircular, a square, a rectangle or a polygon such as a hexagon or an octagon.

Although FIG. 1 shows that the sectional shapes of the rod-shaped device 1 and the hollow section 3h are similar, furthermore, they need not be formed similar. For example, the sectional shape of the rod-shaped device 1 may be circular while that of the hollow section 3h is semicircular or polygonal, and the sectional shape of the rod-shaped device 1 may be semicircular or polygonal while that of the hollow section 3h is circular.

As shown in FIGS. 1B and 1C, an electrode section 3a is formed along the inner surface of this hollow section 3h. This electrode section 3a is formed by the conductive layer 3, and its approximately cylindrical inner surface forms the inner surface of the hollow section 3h. According to FIG. 1, the portion of the hollow section 3h on the side of the tip end of the rod-shaped device 1 rather than the inner bottom surface 3s (the portion of the length L in FIG. 1) forms the electrode section 3a.

The inner surface of the electrode section 3a need not be approximately circular. The sectional shape of the space surrounded by its inner surface may be semicircular, a square, a rectangle or polygonal such as hexagonal or octagonal.

Although FIG. 1 shows the electrode section 3a as being formed by a portion of the conductive layer 3, the electrode section 3a may be formed by another conductive material distinct from the conductive layer 3.

If it is so structured that the insulating layer 4 be formed on the side surface of the shaft member 2 and the conductive layer 3 be formed on its surface, the electrode section 3a may be formed by removing a portion of the insulating layer 4 so as to expose the conductive layer 3 to the hollow section 3h.

If it is so structured that the insulating layer 4 be formed on the side surface of the shaft member 2 and the conductive layer 3 be formed on its surface, furthermore, the electrode section 3a may be provided on the inner surface of the insulating layer 4 with another conductive material distinct from the conductive layer 3 by electrically connecting this electrode section 3a with the conductive layer 3.

As shown in FIG. 1A, a signal detecting section 6 is provided at the base end of the rod-shaped device 1, or the other end opposite from the end section where the electrode section 3a is formed. This signal detecting section 6 is formed by a conductive material and is electrically connected to the conductive layer 3. As a result, if a voltage is applied to the signal detecting section 6, it is possible to apply the voltage to the electrode part 3a through the conductive layer 3.

A portion of the insulating layer 4 may be removed in order to form the signal detecting section 6 with the exposed part. It needs only be connected electrically to the conductive layer 3.

Although the conductive layer 3 is intended to function as a lead line for electrically connecting the signal detecting section 6 with the electrode section 3a, a lead line such as an electrical wire may be provided to the rod-shaped device 1 so as to electrically connect them both, instead of providing the conductive layer 3. If the conductive layer 3 is caused to function as the lead line, however, it becomes possible to make the rod-shaped device 1 thinner, and there is the benefit, as explained above, that a portion of the conductive layer 3 is usable as the electrode section 3a.

Next, a biosensor utilizing the aforementioned rod-shaped device is explained.

When a rod-shaped device according to the present embodiment is used as a biosensor, a sensing substance MS adapted to react with the object under test such as glucose to be detected by this biosensor is disposed inside the hollow section 3h of the rod-shaped device 1, as shown in FIG. 1.

Although glucose oxidase is used as the sensing substance for glucose, any appropriate substance may be used according to the object under test. Examples include enzymes such as glucose oxidase, antigens, antibodies, peptides, receptors, acceptors, nucleic acids, sugar, cells, microorganisms, transmission-selective membranes, membranes for preventing nonspecific absorption, chelate reagents, crown ether and cyclodextrin.

The sensing substance MS may fill the hollow section 3h without leaving any gap but the filling may take place in the shape as shown in FIG. 2A. Explained more in detail, the hollow section 3h may be filled with the sensing substance MS such that a hollow introductory space MH is formed in the axial direction of the rod-shaped device 1, or the axial direction of the hollow section 3h. If the concentration of the object under test is small, a sufficient amount of the sensing substance MS and a sufficient reaction area with the object under test are necessary for an accurate measurement. If an introductory space MH is provided in such a situation, the sensing substance MS and the object under test can be caused to react with each other not only in the opening region at the end but also on the inner surface of the introductory space MH and hence the sensing substance MS and the object under test can be reacted sufficiently and rapidly. Thus, a measurement can be effected with high sensitivity and speedily even where the concentration of the object under test is low.

In particular, if the sensing substance MS to be attached to the surface of the electrode section 3a is formed not as a thin film but as a membrane with a thickness while the introductory space MH is being formed, it is possible to deposit a large amount of the sensing substance MS while increasing the area of the contact region between the object under test and the sensing substance MS by the formation of the introductory space MH. As a result, it becomes possible to keep the sensing substance MS and the object under test reacting with each other sufficiently and to prevent any significant lowering of the detection sensitivity even after the degradation of the sensing substance MS has progressed. This results in improved sensor lifetime for the biosensor.

Moreover, if the introductory space MH is provided, the amount of the sensing substance MS to be used is reduced by the volume of the introductory space MH, as compared to the case where the introductory space MH is not prepared.

This introductory space MH may be formed by a method of any kind. For example, if the method of applying a voltage to the electrode section 3a so as to cause the sensing substance MS to become attached to the electrode section 3a electrically is employed, the introductory space MH can be formed since the sensing substance MS becomes deposited along the electrode section 3a.

Figure 6A:
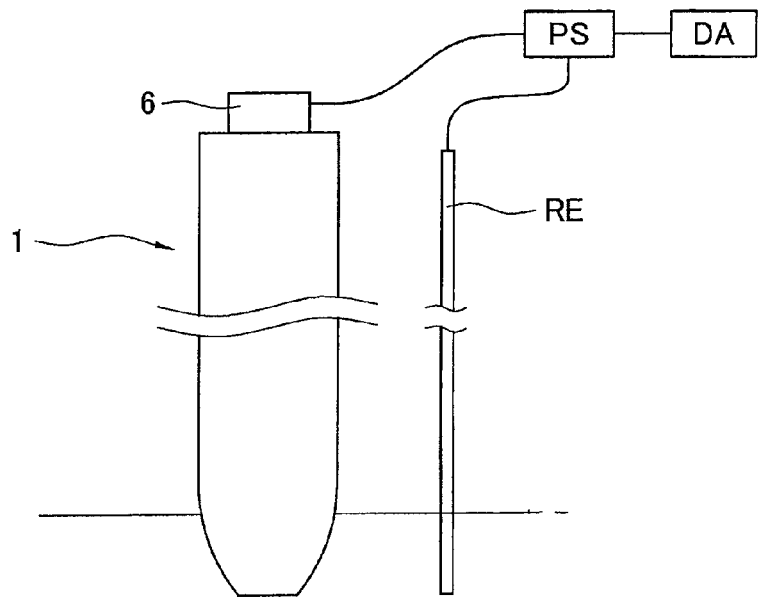
FIGS. 6A and 6B, together referred to as FIG. 6, are schematic diagrams for explaining the measurement of a substance in an organism by the rod-shaped device.

The biosensor serves to oxidize and reduce the reaction product of the object under test and the sensing substance MS at the electrode in contact with the sensing substance MS and to measure the concentration, etc. by detecting the changes in the current and the voltage generated at such a time. Thus, a pair of electrodes becomes necessary in order to apply a voltage to a substance inclusive of the object under test. In the case of a rod-shaped device 1 as shown in FIG. 1, a counter electrode RE must be provided to the electrode section 3a of the rod-shaped device 1 apart from the rod-shaped device 1, as shown in FIG. 6A.

If the counter electrode RE is provided apart from the rod-shaped device 1, there is the advantage of being able to simplify the structure of the rod-shaped device 1.

If the counter electrode RE is provided to the rod-shaped device 1, on the other hand, there is the advantage in that only the rod-shaped device 1 needs be placed to the organism at the time of measurement. Various methods are conceivable for providing a counter electrode RE to the rod-shaped device 1 but if the rod-shaped device 1 is structured as shown below, the counter electrode RE can be provided to the rod-shaped device 1.

Since providing the counter electrode RE to the rod-shaped device 1 means that both electrodes are fixed to the rod-shaped device 1, the distance between the electrode section 3a and the counter electrode RE can always be kept constant and there is the advantage that the condition of measurement becomes stabilized because there is no change in the relative positions of both electrodes and hence the positional relationship between the object under test and both electrodes becomes stable.

Still another advantage of proving the counter electrode RE to the rod-shaped device 1, as compared to the case where the counter electrode RE and the rod-shaped device 1 are separately provided, is that the counter electrode RE can be positioned close to the rod-shaped device 1.

In the situation where the rod-shaped device 1 is used as a biosensor independent of the position of the counter electrode RE, protein, etc. may become attached to the counter electrode RE such that the electrical resistance between the counter electrode RE and the electrode 3a increases and the measurement error may increase. In such a situation, if the counter electrode RE is provided to the rod-shaped device 1, the measurement error can be controlled since the distance between the counter electrode RE and the electrode 3a is small although protein, etc. are attached to the counter electrode RE.

As shown in FIG. 3A, if a conductive layer 5 is provided on the surface of the insulating layer 4, or on the surface of the rod-shaped device 1, such a conductive layer 5 can be used as the counter electrode RE.

As shown in FIG. 2C, if another insulating layer 7 is formed on the surface of the conductive layer 5 and a portion of this conductive layer 5 is exposed inside the hollow section 3h, this exposed portion 5a can be used as the counter electrode RE. It is also feasible to provide an electrode made of a conductive material inside the hollow section 3h and to have this electrode electrically connected to the conductive layer 5.

Figure 4B:
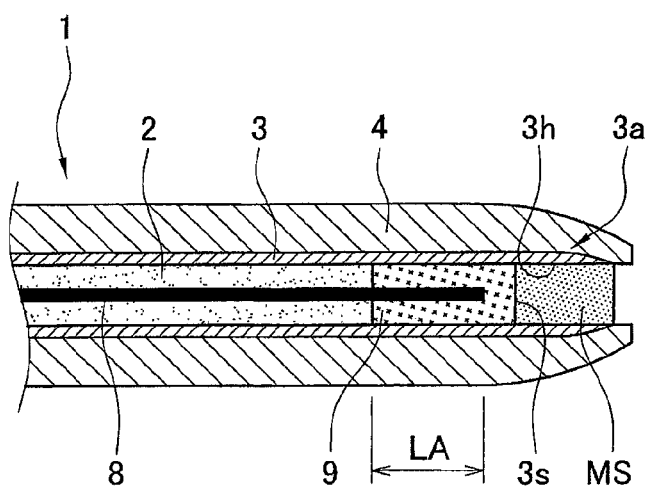

As shown in FIG. 4B, furthermore, if a conductive wire member 8 is provided with an end part disposed inside the hollow section 3h, its portion protruding from the shaft material 2 (the portion with length LA in FIG. 4B) can be used as the counter electrode RE. In this situation, it is preferable to fill the space between the sensing substance MS and the conductive wire member 8 with a material 9 capable of ion exchange, instead of electrically connecting the sensing substance MS and the conductive wire member 8. This material 9 may comprise a polymer electrolyte in a liquid or solid form such as ion-exchange resin Naphion (manufactured by DuPont, Inc, registered trademark).

In this case, it goes without saying that the shaft member 2 must be of an insulating material or that the shaft material 2 and the conductive wire member 8 must be electrically insulated from the conductive layer 3. The conductive wire member 8 is not particularly limited to be of the shape of a rod, a tube, a fin or a rod with a slit.

Figure 5A:
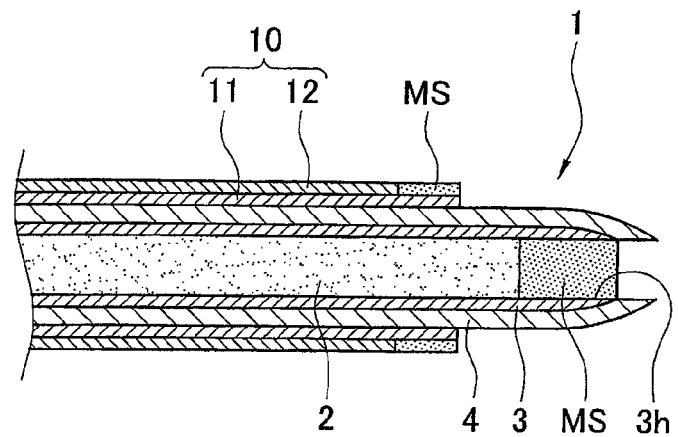
FIGS. 5A and 5B, together referred to as FIG. 5, are schematic enlarged sectional views of end parts of rod-shaped devices according to other embodiments.

Moreover, as shown in FIG. 5A, it is also possible to use the rod-shaped device 1 in combination with a tubular device 10.

In this application, the tubular device 10 comprises a conductive tubular member 11 with a throughhole and having an insulating layer 12 on the surface and the sensing substance MS disposed on the exposed surface of the tubular member 11 where a portion of this insulating layer has been removed. The rod-shaped device 1 is inserted into this throughhole of the tubular member 11 and its end part is protruded from the end of the tubular member 11. The counter electrode RE is disposed near the rod-shaped device 1, and if a voltage is applied between the conductive layer 3 of the rod-shaped device 1 and the counter electrode RE and between the tubular member 11 and the counter electrode RE, it is possible to measure the concentration of the object under test, etc. near the end part of the rod-shaped device 1 and near the position of the tubular member 11 where the sensing substance MS is disposed.

If the sensing substance MS contained in the hollow section of the rod-shaped device 1 and the sensing substance MS provided to the tubular member 11 are different substances, these different substances can be measured at the same.

The tubular member 11 can be used as a reference electrode if no sensing substance MS is provided thereto and the current detected from the rod-shaped device 1 can be corrected on the basis of the current detected from the tubular member 11.

Figure 5B:
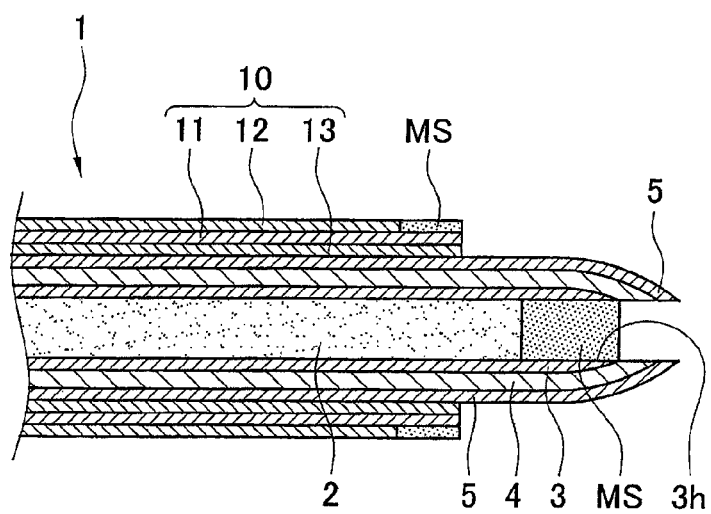

As shown in FIG. 5B, if the rod-shaped device 1 also includes the counter electrode RE (corresponding to the conductive layer 5 in FIG. 5B), there is no need to provide a counter electrode RE separately from the rod-shaped device 1.

Next, examples of use of a biosensor making use of an aforementioned rod-shaped device 1 are explained.

Although situations where the sensing substance MS is glucose oxidase will be explained in what follows, it goes without saying that the quantity, concentration, etc. of a substance corresponding to the sensing substance MS can be detected as in the case of glucose oxidase.

To start, glucose oxidase is placed inside the hollow section 3h of the rod-shaped device 1. Next, as shown in FIG. 6, the rod-shaped device 1 with glucose oxidase provided inside is inserted into an organism. If the shaft diameter of the rod-shaped device 1 is 500 μm or less, preferably 300 μm or less, and more preferably 200 μm or less, it may be penetrated or inserted into, or left buried inside the organism. Moreover, it is possible to reduce the burden imposed on the organism when it is left inside the organism. For example, the generation of pain can be controlled and the wound can be reduced.

Figure 3B:
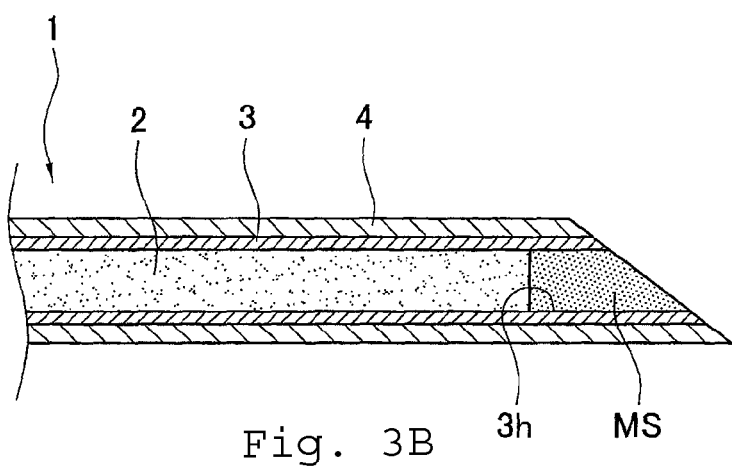
Figure 3C:
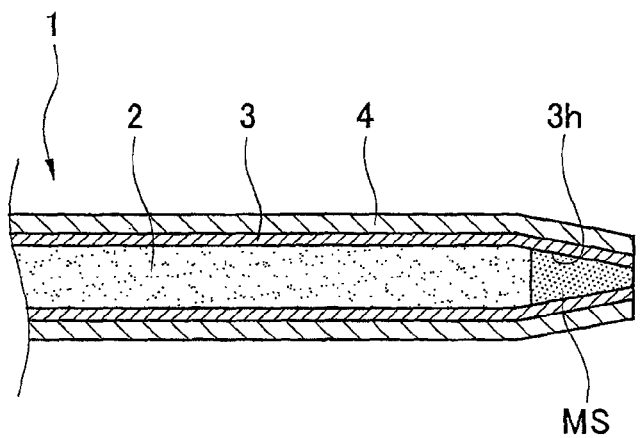

If the end part of the rod-shaped device 1 is shaped so as to become narrower towards the end (as shown in FIG. 3C) or made in a shape of being cut by an inclined plane with respect to the axial direction, or in the shape of a hypodermic needle (as shown in FIG. 3B), the resistance at the time of penetration or insertion can be reduced and the burden imposed on the organism can be reduced.

As shown in FIG. 6A, the signal detecting section 6 of the rod-shaped device 1 is connected to a potentiostat PS and the rod-shaped device 1 is placed at a specified position of the organism to be measured. Next, the counter electrode RE such as a silver-silver chloride electrode connected to the potentiostat PS is placed near the rod-shaped device 1.

Figure 6B:
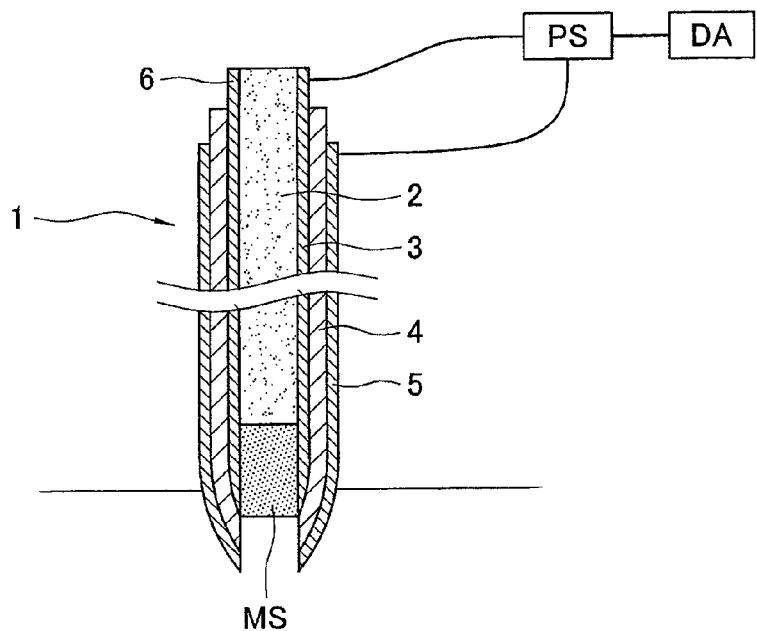

In the case of a rod-shaped device 1 provided with a counter electrode RE, as shown in FIG. 6B, the signal detecting section 6 of the rod-shaped device 1 and the counter electrode RE are connected to the potentiostat PS, and only the rod-shaped device 1 needs be placed at a specified position of the organism.

After the rod-shaped device 1 and the counter electrode RE are placed at their specified positions, a voltage is applied between the conductive layer 3 of the rod-shaped device 1 and the counter electrode RE. The voltage to be applied may be determined appropriately according to the kind of the sensing substance MS and the purpose of the measurement. In the case of a measurement of the glucose concentration by glucose oxidase, for example, if the material for the conductive layer 3 and the counter electrode RE is silver-silver chloride, the voltage to be applied between the two electrodes might be between about −0.5V and +1.0V.

As the voltage is applied between the counter electrode RE and the conductive layer 3 of the rod-shaped device 1, if there is glucose present near the end of the rod-shaped device 1, a reaction takes place between this glucose and glucose oxidase, hydrogen peroxide being generated according to the quantity of glucose. As a result, an oxidation reaction of hydrogen peroxide and a reduction reaction of oxygen take place on the inner surface of the hollow section 3h of the conductive layer 3 (the region with width of L in FIG. 1B). As the oxidation reaction of hydrogen peroxide takes place, there is a change in the current flowing between the signal detecting section 6 of the rod-shaped device 1 and the counter electrode RE according to the quantity of hydrogen peroxide. In other words, the current flowing between the signal detecting section 6 of the rod-shaped device 1 and the counter electrode RE changes according to the quantity of glucose that exists near the end of the rod-shaped device 1.

Thus, if this change in the current is detected by the ammeter of the potentiostat PS or the like and the detected data are analyzed by a data analyzing means DA connected to the potentiostat PS, it is possible to detect the presence or absence of glucose near the end of the rod-shaped device 1 and its quantity and concentration.

In the above, the physical quantity to be detected between the signal detecting section 6 of the rod-shaped device 1 and the counter electrode RE need not be the electric current. A change in voltage may be detected instead, and any optimum quantity may be selected according to the kind of material reacting with the sensing substance MS.

The rod-shaped device 1 according to the present embodiment has an electrode section 3a disposed on the inner surface of the hollow section 3h. Since the electrode section 3a can thus be prevented from contacting the organism as the rod-shaped device 1 is inserted into it, it is possible to prevent damage to the electrode section 3a. Since the sensing substance MS, too, is contained within the hollow section 3h, the sensing substance MS can be prevented from falling off even when the main body is being inserted into the organism.

When the rod-shaped device 1 is placed inside the organism, glucose and glucose oxidase contact each other only at the end opening region of the hollow section 3h. Since the region where the sensing is carried out is reduced, even a very small region can be inspected.

Moreover, since the quantity of the sensing substance MS that is freed and scattered away from the hollow section 3h can be reduced if the end opening region is small, it is possible to improve the useful lifetime of the sensor. In the case where glucose oxidase is maintained in the hollow section 3h, for example, enzymes contained in glucose oxidase and hydrogen peroxide generated by the reaction between glucose and glucose oxidase can be prevented from diffusing into the organism. Since this makes it possible to keep hydrogen peroxide and oxygen at high concentrations within the hollow section 3h, the detection sensitivity and detection accuracy can be improved and the detection period can be made longer.

The hollow section 3h is formed in a cylindrical shape, and the electrode section 3a provided on its inner surface has a cylindrical surface on the side of the hollow section 3h. For this reason, if the rod-shaped device 1 is made thinner or its end opening region is made smaller, the area where the oxidation and reduction reactions take place can be kept large by extending the electrode section 3a in the axial direction of the rod-shaped device 1. In other words, if the length of the electrode section 3a is increased in the axial direction of the rod-shaped device 1, the area of the electrode section 3a can be increased independent of the sectional area of the hollow section 3h (or the diameter of the rod-shaped device 1). Thus, its detection sensitivity and detection accuracy can be maintained high while the sensing region is kept narrow.

If it is possible to increase the area of the electrode section 3a, this means that the area for applying voltage can also be made larger. This makes it possible to allow more current to flow between the counter electrode RE and the electrode section 3a and the sensitivity of the sensor can be improved if this is used for a biosensor. Moreover, the ability to increase the area of the electrode section 3a implies that the quantity of the sensing substance MS near the electrode section 3a can be increased, and this means that the sensor sensitivity can be improved while the response speed of the sensor is kept high.

Moreover, since the end of the electrode section 3a is positioned near the end opening region and the time for hydrogen peroxide generated by the reaction near the end opening region to be reduced becomes shorter, this serves to improve the detection sensitivity. Since the electrode section 3a is cylindrically formed, furthermore, although glucose oxidase in inner parts of the hollow section 3h reacts with glucose, the distance between the location of the reaction and the electrode section 3a is not much different from that if the reaction took place near the end opening region. In other words, even if glucose oxidase in inner parts of the hollow section 3h reacts with glucose, the time from the generation of hydrogen peroxide until it is reduced can be made shorter. Thus, the detection sensitivity can be maintained high even if the sensing substance MS near the end opening region has been deteriorated or the quantity of the object under test is large.

If the length of the hollow section 3h in the axial direction of the rod-shaped device 1 is increased, furthermore, it is possible to increase the volume of the hollow section 3h independent of the sectional area of the hollow section 3h (or the diameter of the rod-shaped device 1). Since it is possible, therefore, to increase the quantity of the sensing substance containable inside the hollow section 3h while the rod-shaped device 1 is made thinner, it is possible to increase the quantity of the sensing substance inside the hollow section 3h sufficient for the detection of the object under test for a long period of time, and this can improve the useful lifetime of the sensor.

If the shaft member 2 is not provided and the hollow section 3h forms a throughhole from the end of the rod-shaped device 1 to its base end, it becomes possible to fill the sensing substance from the base end of the rod-shaped device 1 into the hollow section 3h and hence the sensor can be used continuously over a long period of time.

In a situation where the hollow section 3h is formed such that its inner bottom surface 3s serves as the front end surface of the shaft member 2, if the shaft member 2 comprises a material with high heat transmissivity, it is possible to heat the substance inside the hollow section 3h through the shaft member 2. If the shaft member 2 comprises optical fibers, etc., it also becomes possible to apply light to the substance inside the hollow section 3h through the shaft member 2. In this way, an optical stimulus can be applied to the sensing substance MS inside the hollow section 3h. Thus, the rod-shaped device 1 can be used as a device for administering a medicine at a specified position within an organism or, in reverse, as a device for collecting cells and tissues from a specified position within an organism.

Figure 7A:
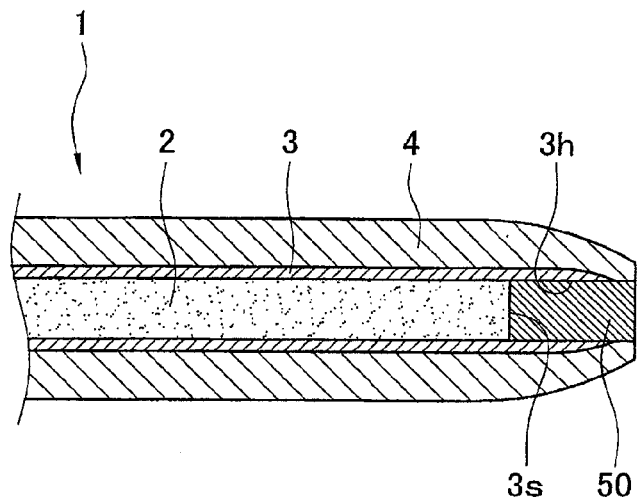
FIG. 7A is a drawing that shows an example of method for using the rod-shaped device.
Figure 7B:
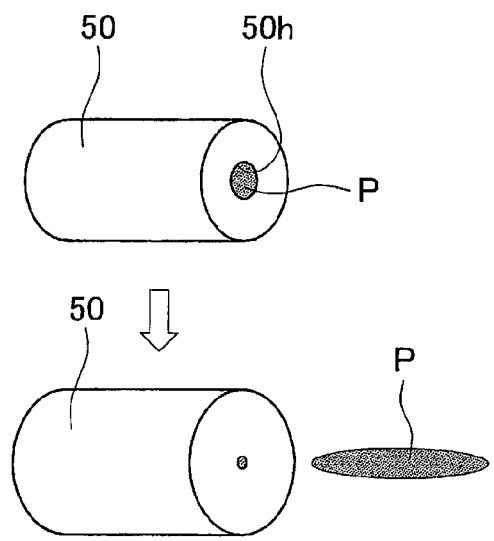
FIG. 7B is a drawing that shows the manner in which a reagent P is being injected from a cylindrical container.

A cylindrical container 50 is formed, for example, with a material which changes its volume by heat or light, say, by expanding or shrinking by heat or light, as shown in FIG. 7A. A medicine P or the like is contained within a cavity 50h of this cylindrical container 50 and this cylindrical container 50 is placed inside the hollow section 3h. If the end of the rod-shaped device 1 is placed at the location where it is desired to administer the medicine P and heat or light is applied to the cylindrical container 50, it is possible to deform the cylindrical container 50 such that the medicine P or the like inside the cavity 50h can be caused to be emitted out from the end of the rod-shaped device 1, as shown in FIG. 7B. In this manner, the medicine P can be reliably administered at the desired position.

Figure 8A:
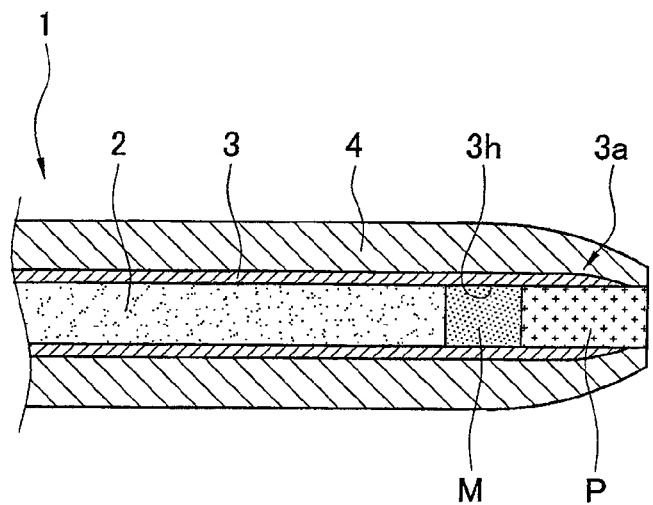
FIGS. 8A and 8B, together referred to as FIG. 8, and FIGS. 9A and 9B, together referred to as FIG. 9, show how a rod-shaped device may be used.
Figure 8B:
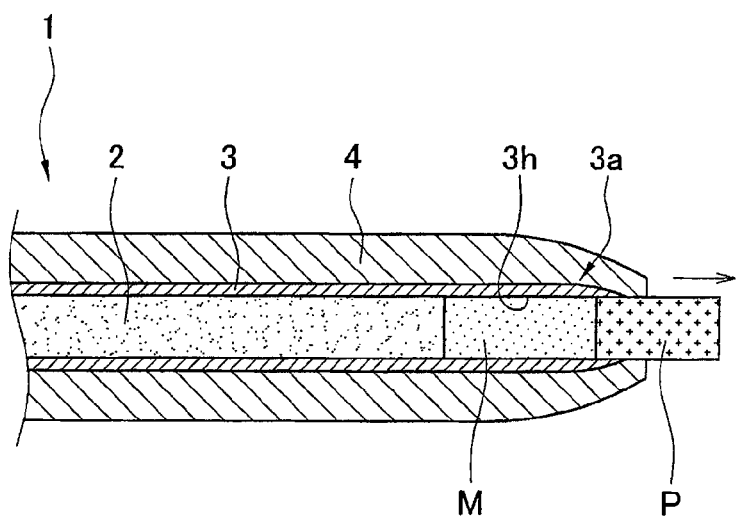

A medicine P or the like is contained in the hollow section 3h and a matter M, which increases its volume by a change in temperature, pH or molecular structure as heat, light or electricity is applied, is placed between this medicine P and the end surface of the shaft member 2, as shown in FIG. 8. If the end of the rod-shaped device 1 is placed at the position where it is desired to administer the medicine P and heat, light or electricity is supplied from the shaft member 2 to the interior of the hollow section 3h, or the matter M, the volume of the matter M can be increased and the medicine P or the like can be emitted out from the end of the rod-shaped device 1, as shown in FIG. 8B, or the medicine P or the like can be reliably administered at the desired position.

Instead of the matter M, another kind of matter which lowers its affinity with the medicine P if heat, light or electricity is applied may be contained. It is then possible by applying heat, light or electricity to such a matter, to have the medicine P emitted out. If another kind of matter which increases affinity with the medicine P as heat, light or electricity is applied is contained, instead of a matter which lowers its affinity with the medicine P when heat, light or electricity is applied, if heat, light or electricity is applied to it before the emission of the medicine P, it goes without saying that the medicine P can be emitted out by preliminarily applying heat, light or electricity before the emission of the medicine P and stopping the application when the medicine P is to be emitted out such that the affinity of this material and the medicine P is lowered.

Figure 9A:
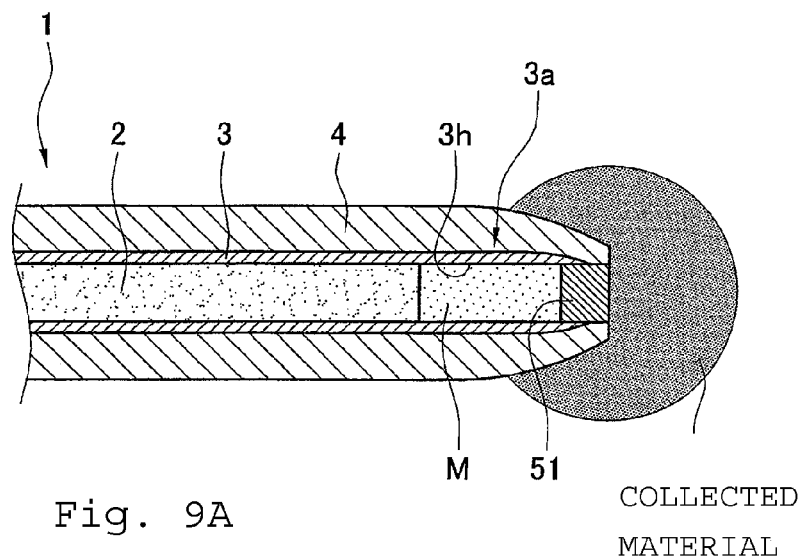
Figure 9B:
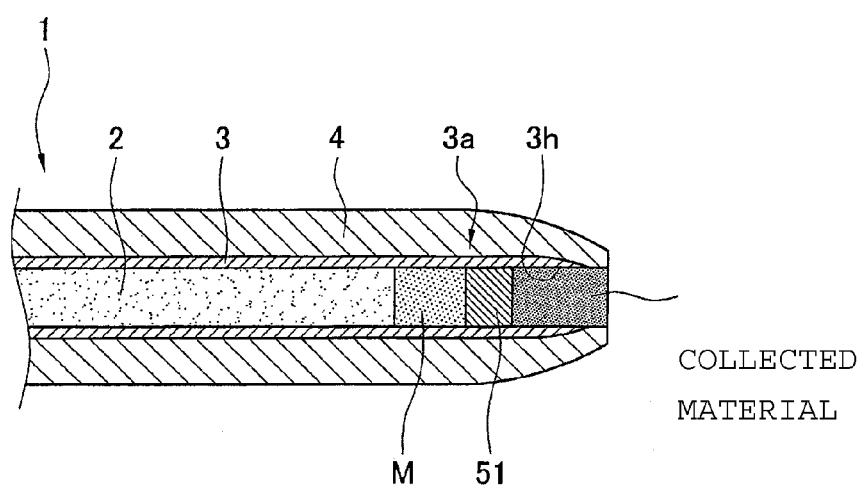

According to another method, as shown in FIG. 9, a plug 51 is provided to hermetically separate the interior of this hollow section 3h and the exterior and a material M, which increases its volume by a change in temperature, pH or molecular structure when heat, light or electricity is applied, is contained between this plug 51 and the front end surface of the shaft member 2 under a condition of heat, light or electricity being applied. In order to maintain this condition, heat, light or electricity is appropriately supplied from the shaft member 2 into the hollow section 3h, or to the material M. If the end part of the rod-shaped device 1 is then placed at the position where it is desired to collect cells, etc. and heat, light or electricity is removed from the material M through the shaft member 2, the volume of the material M can be reduced. As a result, the pressure between the plug 51 and the front end surface of the shaft member 2 is lowered, and since the plug 51 will move towards the front end surface of the shaft member 2, the matter to be collected such as cells near the end of the rod-shaped device 1 can be sucked into the space created by the displacement of the plug 51 in the hollow section 3h. If the matter M, which increases its volume when heat, light or electricity is applied, is replaced by another matter which decreases its volume by a change in temperature, pH or molecular structure when heat, light or electricity is applied, on the other hand, it is possible to apply heat, light or electricity to lower the pressure between the plug 51 and the front end surface of the shaft member 2 so as to move the plug 51 towards the front end surface of the shaft member 2 and to thereby cause the matter to be collected such as cells near the end of the rod-shaped device 1 to be sucked into the space created by the displacement of the plug 51 in the hollow section 3h.

Moreover, still another kind of matter that improves its affinity to the matter to be collected when heat, light or electricity is applied may be contained, instead of aforementioned matter M, and heat, light or electricity may be applied to this matter so as to improve its affinity to the matter to be collected and to have the latter sucked. Instead of this material that improves its affinity to the matter to be collected when heat, light or electricity is applied, still another material that lowers its affinity to the matter to be collected when heat, light or electricity is applied may be contained instead and heat, light or electricity may be kept applied before the matter to be collected is sucked. If the application is stopped at the time of sucking, the affinity between this matter and the matter to be collected is improved and the matter to be collected is sucked.

If the cylindrical container 50 and the material contained in the hollow section 3h have the characteristic of changing its volume by an electrical stimulus, the function described above can be achieved by an electrical stimulus from the electrode section 3a alone.

Next, materials comprising each component of the rod-shaped device 1 are explained.

The shaft member 2 may comprise an insulating material such as super-elastic resin, PET, polyphenylene diamine, polyurethane, nylon, vinyl polychloride, polysiloxane, glass ($SiO_2$), polypropylene, polythiophene, polyester, polyethylene, urea resins, polysilane. polyaniline, metal oxides and alloys, but there is no particular limitation.

If super-elastic resin is used, in particular, the rod-shaped device 1 can be prevented more reliably from bending or becoming damaged when it is penetrated into the object under test while it is being rotated around its central axis because the elasticity of super-elastic resins is particularly high such that the rod-shaped device 1 can be more reliably inserted into the object under test such as organisms. Preferable examples of super-elastic resin include polyisoprene, styrene-butadien copolymers, polyethylene, fluorine resins, polyethylene+nylon, polyethylene+perprene, esters of polyacrylic acid, esters of polymethacrylic acid, polysiloxane, silicon resins, vinyl polychloride, polyethylene chloride, perprene, polyethylene+vinyl polychloride, polyethylene+fluorine resin, polyurethane, polyimide, polyamide and polysilane. In particular, fluorine resins and polysiloxane, which are not easily rejected by organisms, having fitness to organisms, are preferred.

Materials such as optical fibers that are transparent to light and those that can be used for the conductive layer 3, as will be described below, may be used to form the shaft member 2. If use is made of a super-elastic alloy, which is a material usable for the conductive layer 3, as will be explained below, in particular, since the elasticity of super-elastic alloys is very high, the rod-shaped device 1 can be prevented more reliably from bending or becoming damaged when it is penetrated into the object under test while it is being rotated around its central axis, as was the case with the use of super-elastic resins as explained above, such that the rod-shaped device 1 can be more reliably inserted into the object of test such as organisms.

Moreover, if the shaft member 2 is formed by using a conductive material such that the sensing substance MS contacts the front end of the shaft member 2, the inner bottom surface 3s of the hollow section 3h can also be made to function as an electrode. In this way, the area where oxidation and reduction reactions take place can be made still larger and the detection sensitivity and detection accuracy of the sensor can be maintained higher.

The conductive layers 3 and 5 are formed on the outer peripheral surfaces of the shaft member 2 and the insulating layer 4 by a thin film method such as the vapor deposition method, the sputtering method and the electroless plating method although the method of forming the conductive layers 3 and 5 is not limited to these methods and any method may be used for the purpose.

Examples of the material that may be used for the conductive layers 3 and 5 include super-elastic alloys, gold, silver, copper, platinum, alloys such as platinum-iridium alloy, palladium, nickel, titanium, carbon, polypyrol, polythiophene, polyaniline and polyacetylene, but there is no particular limitation.

If use is made of a super-elastic alloy as the material for the conductive layers 3 and 5, in particular, since the elasticity of super-elastic alloys is very high, not only the shaft member 2 but also the conductive layers 3 and 5 can support the force applied to the rod-shaped device 1 and hence the rod-shaped device 1 can be prevented more reliably from bending or becoming damaged when it is penetrated into the object under test while it is being rotated around its central axis, such that the rod-shaped device 1 can be more reliably inserted into the object of test such as organisms. Preferable examples of super-elastic alloy include titanium-nickel alloys (Ti—Ni), indium-thallium alloys (In—Tl), copper-zinc alloys (Cu—Zn), copper-zinc-X alloys (Cu—Zn—X(Si, Sn, Al, Ga)), copper-aluminum-nickel alloys (Cu—Al—Ni), copper-gold-zinc alloys (Cu—Au—Zn), copper-tin alloys (Cu—Sn), nickel-aluminum alloys (Ni—Al), iron-platinum alloys (Fe—Pt), indium-cadmium alloys (In—Cd), manganese-copper alloys (Mn—Cu), silver-cadmium alloys (Ag—Cd), gold-cadmium alloys (Au—Cd), iron-palladium alloys (Fe—Pd), iron-nickel-cobalt-titanium alloys (Fe—Ni—Co—Ti), iron-nickel-carbon alloys (Fe—Ni—C), iron-manganese-silicon alloys (Fe—Mn—Si), titanium-aluminum-tin-zirconium-molybdenum alloys (Ti—Al—Sn—Zr—Mo), titanium-aluminum-vanadium alloys (Ti—Al—V), titanium-molybdenum-aluminum alloys (Ti—Mo—Al), titanium-niobium alloys (Ti—Nb), titanium-niobium-tin alloys (Ti—Nb—Sn), and titanium-vanadium-iron-aluminum alloys (Ti—V—Fe—Al). In particular, alloys not containing copper, nickel and cadmium which are harmful to organisms are preferred.

When platinum is used as material for the conductive layers 3 and 5, if the conductive layers 3 and 5 of platinum are formed after a layer of a different material is formed as substrate prior to the formation of the platinum layer, it is possible to improve the adhesive characteristic of platinum.

The insulating layers 4 and 7 are formed on the surfaces of the conductive layers 3 and 5 by a thin film method such as the vapor deposition method and the sputtering method but their formation is not limited to these methods, and any suitable method may be used for the purpose.

The insulating layers 4 and 7 are formed by using a material with an insulating characteristic that is equivalent to that of the shaft member 2 such as super-elastic resins, PET, polyphenylene diamine, polyurethane, nylon, vinyl polychloride, polysiloxane, glass ($SiO_2$), polypropylene, polythiophene, polyester, polyethylene, urea resins, polysilane, polyaniline and metal oxides, but there is no particular limitation.

Next, an example of the production method of the rod-shaped device 1 is explained.

Figure 10A:
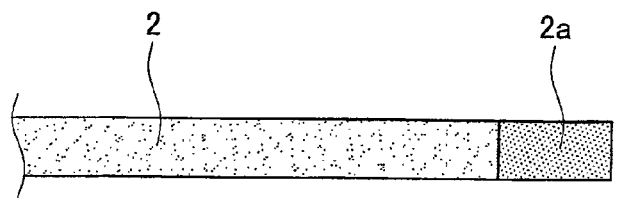
FIGS. 10A, 10B, 10C and 10D, together referred to as FIG. 10, show a production process of the front end part of the rod-shaped device of the same embodiment.

Firstly, a member 2a which is to become the center member is placed on the front end surface of the rod-shaped device 1, as shown in FIG. 10A.

Figure 10B:
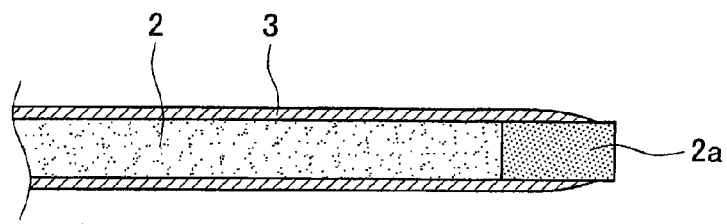

Next, the conductive layer 3 is formed by attaching a conductive material by a method such as sputtering on the outer peripheral surface of the shaft member 2 and the outer peripheral surface of the member 2a. This is done such that this conductive material will become attached within a range that is slightly inward from the front end of the member 2a, as shown in FIG. 10B.

If the conductive layer 3 is intended to be exposed at the front end of the rod-shaped device 1, however, the conductive matter is attached to the front end of the member 2a.

Figure 10C:
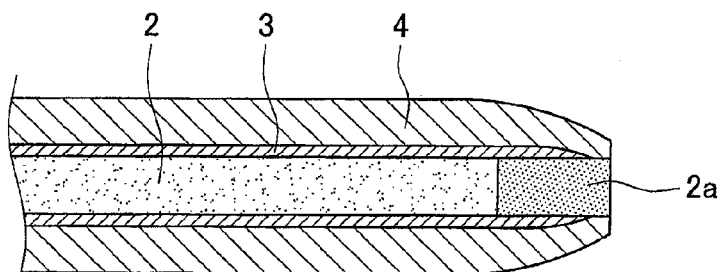
Figure 10D:
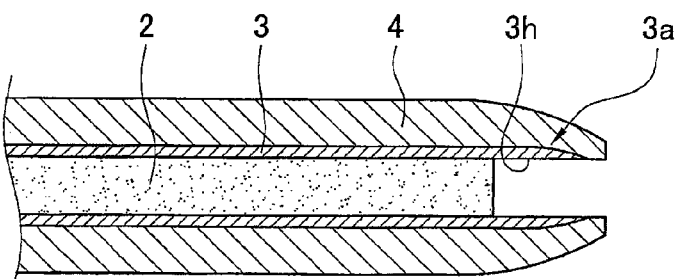

Next, the insulating layer 4 is formed by attaching an insulating material by a method such as sputtering on the outer peripheral surface of the conductive layer 3. The insulating layer 4 is formed so as to completely cover the front end of the conductive layer 3, as shown in FIG. 10C. If the conductive layer 3 is intended to be exposed at the front end of the rod-shaped device 1, however, the insulating layer 4 is formed so as not to completely cover the front end of the conductive layer 3.

Lastly, the member 2a is removed to form the hollow section 3h. The electrode section 3a is formed by the conductive layer 3 on the inner surface of the hollow section 3h.

Figure 11A:
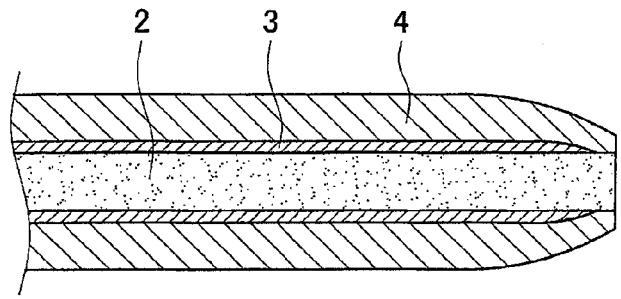
FIGS. 11A, 11B and 11C, together referred to as FIG. 11, show another production process of the front end part of the rod-shaped device of the same embodiment.
Figure 11B:
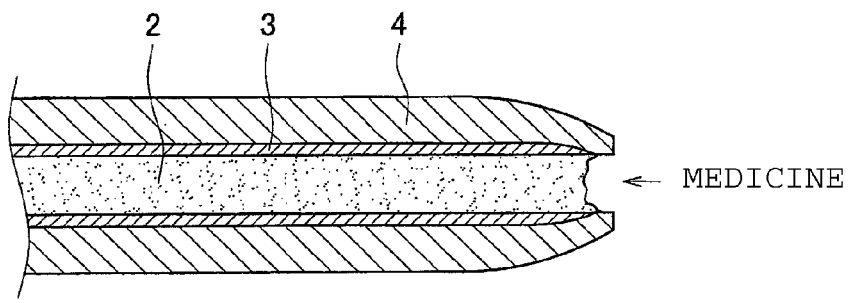
Figure 11C:
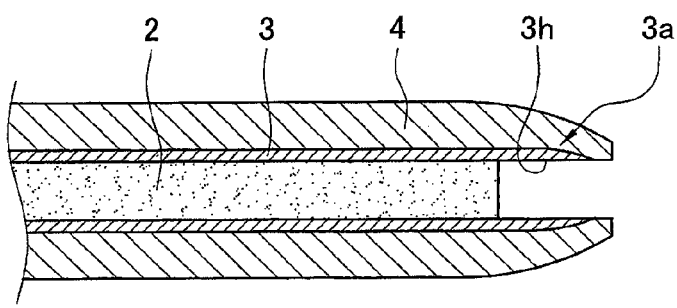

The rod-shaped device 1 may be formed without using the member 2a to serve as the center member at the front end of the shaft member 2. In this case, as shown in FIG. 11A, the front end of the shaft member 2 will continue to the front end of the insulating layer 4 when the insulating layer 4 has been formed but the hollow section 3h may be formed by a mechanical fabrication method if the diameter of the shaft member is large and by a chemical fabrication method if the diameter of the shaft member is small. In the case of a chemical fabrication method, a chemical agent for dissolving the shaft member 2 is applied to its front end, as shown in FIG. 11B, to form the hollow section 3h where the shaft member 2 has been dissolved, as shown in FIG. 11C. Although it is difficult by such a chemical fabrication method to control the depth of the hollow section 3h, a specified depth can be obtained by adjusting the kind of the chemical to be used and the dissolving time.

It now goes without saying that the chemical to be used for dissolving the shaft member 2 should be selected among those which does not dissolve the conductive layer 3 and the insulating layer 4. When a conductive layer 3 is formed with Pt on the surface of a shaft member 2 made of Ni—Ti and an insulating layer 4 is formed with silica, for example, nitric acid may be used to dissolve only the shaft member 2 to form a hollow section 3h.

The shaft member 8 of the rod-shaped device 1 itself may be formed with a material that can be used for forming the conductive layer 3 as explained above. In such a case, the conductive layer 3 becomes unnecessary, and the rod-shaped device 1 becomes completed if only the insulating layer 4 is formed so as to cover the surface of the shaft member 2 and a hollow section 3*h* is formed to the shaft member 2 itself so as to have an electrode section 3*a* on its inner surface. In this way, the rod-shaped device 1 can be made thinner by the thickness of the conductive layer 3 while having the same function as a rod-shaped device 1 having a conductive layer 3 provided. If the diameter of the shaft member 2 is 0.1 µm and that of the insulating layer 4 is also 0.1 µm, even a rod-shaped device 1 with diameter as small as 0.3 µm can be formed. Moreover, since the step of forming the conductive layer 3 becomes unnecessary, the total number of production steps can be reduced. Although the formation of the hollow section 3*h* is difficult also in this case, a mechanical fabrication method is possible if the diameter of the shaft member 2 is sufficiently large and a chemical fabrication method as explained above is still possible if the diameter of the shaft member 2 is small.

After the shaft member 2 of the rod-shaped device 1 is formed with a material that can be used for the conductive layer 3, it is still possible to also form a conductive layer 3 on its surface. If the conductive layer 3 in this case is formed by using a material with higher conductivity than the material for the shaft member 2, it is possible to provide a rod-shaped device 1 with a sufficient strength by means of the material of the shaft member 2 and with a high conductivity by means of the material of the conductive layer 3.

A biosensor 30 may be formed by providing a part which becomes a base (hereinafter referred to simply as the base 35) and a contact section 31. The structure of the contact section 31 and its material are the same as those of the front end part of the rod-shaped device 1 as explained above.

Figure 12A:
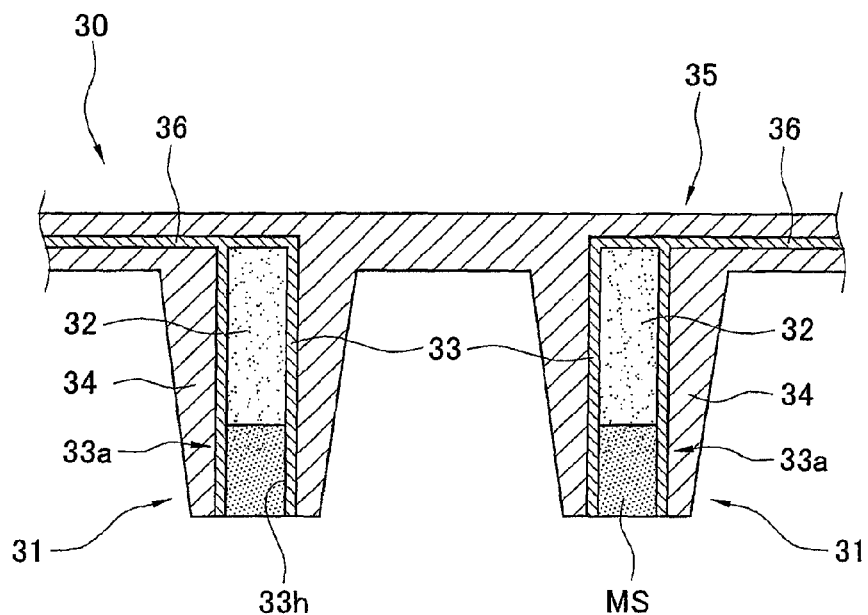
FIGS. 12A and 12B, together referred to as FIG. 12, are schematic diagrams of a biosensor having a contact section.

As shown in FIG. 12, the biosensor 30 is provided with a base 35 in the form of a sheet or a plate. This base 35 is formed of a material such as an insulating film or synthetic resin, an insulating fiber material or a metallic material having an insulating membrane. Various materials such as those with high rigidity, pliability or flexibility, or super-elastic materials, as well as those usable for the shaft member 2 and the insulating layer 4 of the rod-shaped device 1 can be used.

The base 35 need not be in the shape of a sheet or a plate but may be in the shape of a suction cup or a block, not being limited as to its shape. The contact section 31 of the biosensor 30 may be disposed so as to be uniformly distributed over the surface of the base 35 or only partially in the case of an annular or linear placement. If the base 35 is in the shape of a suction cup, for example, it is effective to place the contact section 31 near the center of the surface of the suction cup such that the sucking force of the suction cup can be utilized effectively for the biosensor 30.

If the counter electrode is to be arranged separately from the contact section 31 in the biosensor 30, the counter electrode may be placed on the base 35 where the contact section 31 is not. The counter electrode and the contact section 31 can be freely arranged according to the object under test, for example, by arranging the contact section 31 annually and the counter electrode at its center, by placing the contact section 31 at the center of the annually arranged counter electrode, or by arranging the counter electrode and the contact section 31 alternately. The measurement error can be reduced since the counter electrode and the contact section 31 can be affixed in an optimized way in the biosensor 30.

A conductive section 36 is provided inside or on the surface of the base 35, being formed of a conductive material such as the material used for the conductive layer 3 of the rod-shaped device 1 described above and being electrically connected to a conductive layer 33 of the contact section 31, to be explained below. It now goes without saying that a pliable and flexible material should be used for the conductive section 36 if the base 35 is of a pliable and flexible material.

A plurality of such conductive sections 36 may be provided. If there are a plurality of conductive layers 33 in the contact section 31 and each of the plurality of conductive sections 36 is connected to a corresponding one of the conductive layers 33, it is convenient because one of the conductive layers 33 can be used as a counter electrode or a reference electrode.

FIG. 12 shows a contact section 31 formed so as to protrude from one of the surfaces of the base 35. This contact section 31 has substantially the same structure as the front end part of the rod-shaped device 1 described above, having a shaft member 32 and a conductive layer 33 and an insulating layer 34 alternately formed on its side surface.

The shaft member 32, the conductive layer 33 and the insulating layer 34 may each be of the same material as the shaft material 2, the conductive layer 3 and the insulating layer 4 described above, respectively.

The contact section 31 has a cylindrical hollow section 33*h* formed inwardly indenting from its front end surface and a cylindrical electrode section 33*a* is provided on the inner surface of the hollow section 33*h*. The sensing substance MS is disposed inside the hollow section 33*h*.

As in the case of the rod-shaped device 1, the electrode section 33*a* may be formed as a part of the conductive layer 33 or by way of a conductive member separate from the conductive layer 33 but electrically connected to the conductive layer 33. Moreover, a lead line may be provided instead of the conductive layer 33, the electrode section 33*a* and the conductive section 36 being electrically connected.

If the base 35 of the biosensor 35 is formed with a member in the shape of a sheet, the contact section 31 contacts an organism and penetrates it if the biosensor 30 is attached to the surface of the organism such that its contact section 31 is on the side of the organism. Then, as in the case of the rod-shaped device 1 described above, if the counter electrode is placed near the contact section 31, a voltage can be applied between the counter electrode and the conductive section 36, or between the counter electrode and the electrode section 33*a*, that is, a current can be made to flow to the material between them. Thus, a current value corresponding to the concentration or the quantity of the material between the counter electrode and the electrode section 33*a* can be detected.

The counter electrode separated from the biosensor need not be provided if there are a plurality of conductive layers 33 and one of them is used as the counter electrode.

Figure 12B:
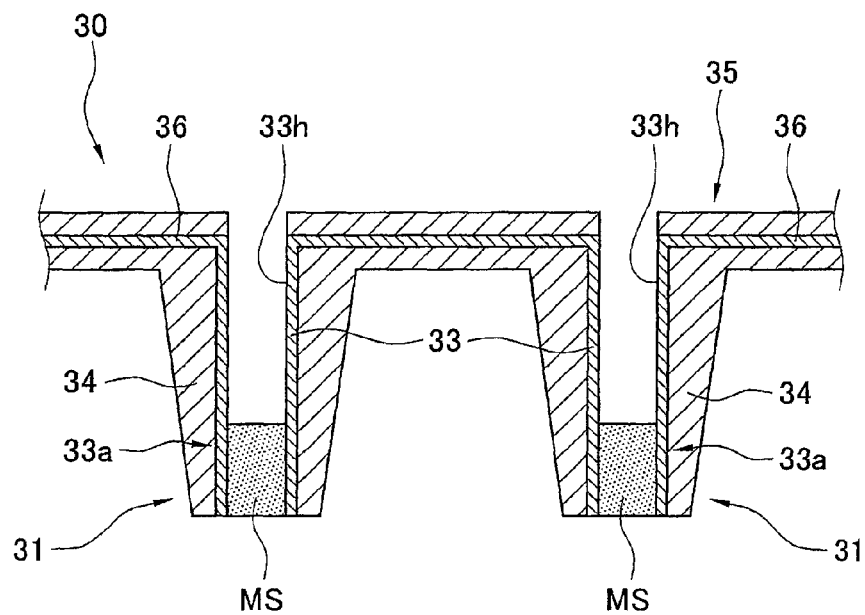

If the shaft member 32 is not provided but the hollow section 33*h* is a throughhole that penetrates from the front end to the base end of the contact section 31, as in the case of the rod-shaped device 1, the sensing substance may be filled from the base end of the contact section 31 into the hollow section 33*h*, as shown in FIG. 12B.

If the shaft member 32 of the contact section 31 is formed with a conductive material, the inner bottom surface of the hollow section 33*h* can also be made to function as an electrode, as in the case of the rod-shaped device 1. In this way, the area for carrying out the oxidation and reduction reactions can be even larger and the detection sensitivity and the detection accuracy of the sensor can be maintained at a high level.

If the shaft member 32 of the contact section 31 is formed with a material with high heat conductivity, it is possible to heat the material inside the hollow section 33*h*, and if the shaft member 32 is formed with a material such as optical fibers, it is also possible to irradiate light on the material inside the hollow section 33*h*. Then, as in the case of the rod-shaped device 1 described above, it becomes possible to use the biosensor 30 as a device for administering a medicine or the like at a specified position inside an organism or collecting cells or a tissue at the specified position inside an organism by placing a cylindrical container 50 or the material M described above, as shown in FIGS. 7, 8 and 9.

Next, a tubular device as another embodiment of the biodevice of this invention and a biosensor comprising such a tubular device are explained.

Figure 13A:
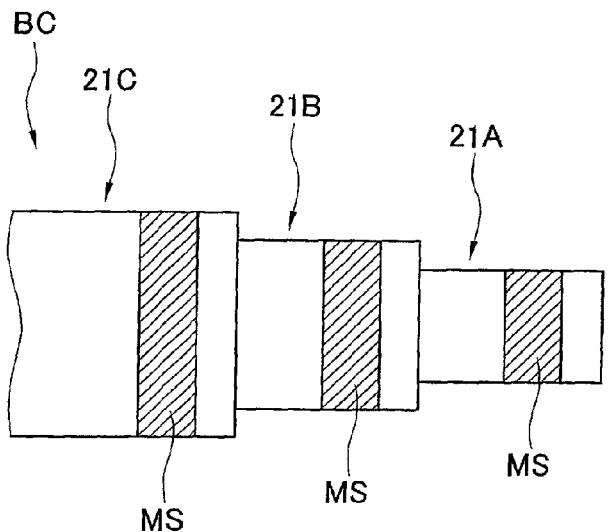
FIG. 13, consisting of FIGS. 13A and 13B, shows a biosensor according to this invention, FIG. 13A being an enlarged schematic side view of its front end part and FIG. 13B being its enlarged schematic sectional view.
Figure 13B:
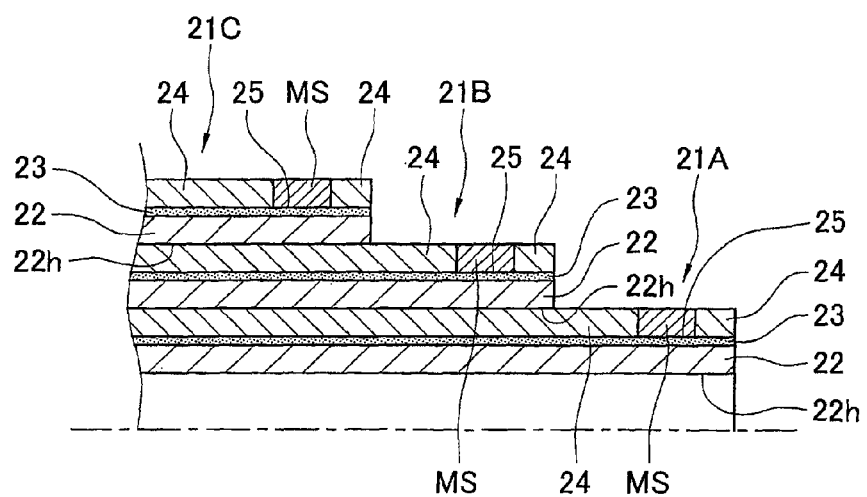

FIG. 13, is a schematic diagram of a biosensor BC according to this embodiment, FIG. 13A being an enlarged schematic side view of its front end part and FIG. 13B being its enlarged schematic section view. FIG. 14 is a schematic side view of this biosensor BC.

The size and the relative ratio of thickness and length of each component are not necessarily accurately represented. In the case of a tubular device of this invention as shown in FIGS. 13 and 14, if its outer diameter is about 0.3µ-6 mm, it is preferable that the outer diameter of the tubular member 22 be about 0.1 µm-5 mm and its thickness be about 0.01 µm-2 mm, the thickness of the conductive layer 23 be about 0.05 µm-100 µm and the thickness of the insulating layer 24 be about 0.05-700 µm, but the shaft diameter of the tubular member 22 and the thicknesses of the conductive layer 23 and the insulating layer 24 are not intended to be limited within these ranges. The conductive layer 23 and the insulating layer 24 may be of the same thickness but if the conductive layer 23 is made thinner than the insulating layer 24, it is possible to reduce the possibility of short-circuiting of the conductive layer 23 with another material while preventing the outer diameter of the main body 21 from becoming too thick.

The biosensor BC according to this embodiment comprises a plurality of tubular devices 21A-21C having hollow throughholes, as shown in FIGS. 13 and 14, being structured as a combination of these three tubular devices 21A-21C.

These tubular devices 21A-21C are structured substantially identically, the outer diameter ODA of tubular device 21A being smaller than the inner diameter IDB of the throughhole through tubular device 21B and the outer diameter ODB of tubular device 21B being smaller than the inner diameter IDC of the throughhole through tubular device 21C. Their lengths are such that they become shorter in the order of tubular device 21A, tubular device 21B and tubular device 21C, but there is no limitation on their individual lengths.

Tubular device B is inserted into the throughhole through tubular device C, and tubular device A is inserted into the throughhole through tubular device B. Thus, the biosensor BC of this embodiment has the three tubular devices 21A-21C having different outer shapes in a nesting structure.

For forming this nesting structure, the outer diameter OD of a tubular device to be inserted and the inner diameter ID of the throughhole accepting it need only to be sufficiently different such that the insertion can be effected smoothly. These is no particular limitation as to this difference but it is preferably about 5-100 µm such that a damage to the insulating layer 24 due to the insertion can be prevented.

Although an example is shown with three tubular devices 21A-21C combined together, this is not intended to limit the scope of the invention. Two or four or more tubular devices may be combined to form a biosensor of this invention.

An electrode section 25 is formed on the outer surface of an end part of each of the tubular devices 21A-21C. A sensing substance MS adapted to react with the object under test of the biosensor BC is displaced at this electrode section 25. Examples of this sensing substance MS include enzymes such as glucose oxidase, antigens, antibodies, peptides, receptors, acceptors, nucleic acids, sugar, cells, microorganisms, transmission selective membranes, membranes preventing nonspecific absorption, chelate reagents, crown ether and cyclodextrin.

Next, an example of using the biosensor BC of this embodiment is explained for a situation where the sensing substance MS is glucose oxidase but it goes without saying that the quantity and concentration of objects corresponding to other sensing substances MS can similarly be detected.

Firstly, tubular devices 21A and 21B are arranged as shown in FIG. 13A such that tubular device 21A protrudes outward from an end of tubular device 21B and tubular device 21B protrudes outward from an end of tubular device 21C. Under this condition, glucose oxidase serving as the sensing substance MS is placed at the electrode sections 25 of tubular devices 21A and 21B. Nothing is placed at the electrode section 25 of tubular device 21C.

The biosensor BC of this embodiment is then placed inside an organism and is adjusted such that the electrode sections 25 of the two tubular devices 21A and 21B will each be at a corresponding measurement position within the organism.

Next, a voltage is applied between signal detecting sections 26 of tubular devices 21A and 21C such that a current flows through the signal detecting section 26, the conductive layer 23 and the electrode section 25 of tubular device 21A, the organism, and the electrode section 25, the conductive layer 23 and the signal detecting section 26 of tubular device 21C, in this order.

Another voltage is similarly applied between signal detecting sections 26 of tubular devices 21B and 21C such that a current flows from signal detecting section 26 of tubular device 21B to signal detecting section 26 of tubular device 21C. Since the tubular members 22 of the tubular devices 21A-21C are made of an insulating material and the outermost layer of tubular device 21C to be explained below is an insulating layer 24, the probability of occurrence of short-circuiting between the conductive layers 23 of mutually adjacent tubular members 21 is reduced.

If glucose is present near the electrode sections 25 of tubular devices 23A and 21B when the voltage is applied to tubular devices 21A-21C as above, it reacts with glucose oxidase and generates hydrogen peroxide according to its amount. This causes an oxidation reaction of hydrogen peroxide and a reduction reaction of oxygen on the surfaces of the electrode sections 25, and as these reactions take place, there is a change in the currents flowing between the signal detection sections 26 of tubular devices 21A and 21B and tubular device 21C. This is to say that the currents that flow between the signal detection sections 26 of tubular devices 21A and 21B and the signal detection section 26 of tubular device 21C according to the quantities of glucose near the electrode sections 25 of tubular device 21A and 21B.

Thus, the presence or absence of glucose, its amount and concentration near the electrode sections 25 of tubular devices 21A and 21B can be detected. Moreover, since the electrode sections 25 of tubular devices 21A and 21B are located at different positions, the differences in the concentration and quantity of glucose according to the difference in location, or their distributions in an organism can be studied.

As for the voltage to be applied between the signal detection sections 26, an optimum value may be selected according to the kind of material that reacts with the sensing substance MS.

The physical quantity to be detected between the signal detection sections 26 of tubular devices 21A and 21B and the signal detection section 26 of tubular device 21C need not be the current but may be the change in the voltage difference.

An optimum physical quantity may be selected according to the kind of the object under test and the purpose of the measurement.

Moreover, different sensing substances MS may be placed in tubular devices 21A and 21B. In this manner, a plurality of materials may be measured at the same time.

If each of the tubular devices 21A-21C of the biosensor BC is arranged so as to be mutually adjustable freely in their axial direction, the positions of the electrode sections 25 of tubular devices 21A and 21B can be selected more accurately at their desired positions.

If the tubular devices 21A-21C are arranged such that their relative positions cannot be changed, on the other hand, the relative positions of their electrode sections 25 can be held fixed and hence the concentration of glucose, etc. at positions separated always by a constant distance can be measured. The relative positions may be fixed by any method. If an insulating member 27 is used as shown in FIG. 15B, organisms can be prevented from entering the gaps between the tubular devices 21.

Figure 16A:
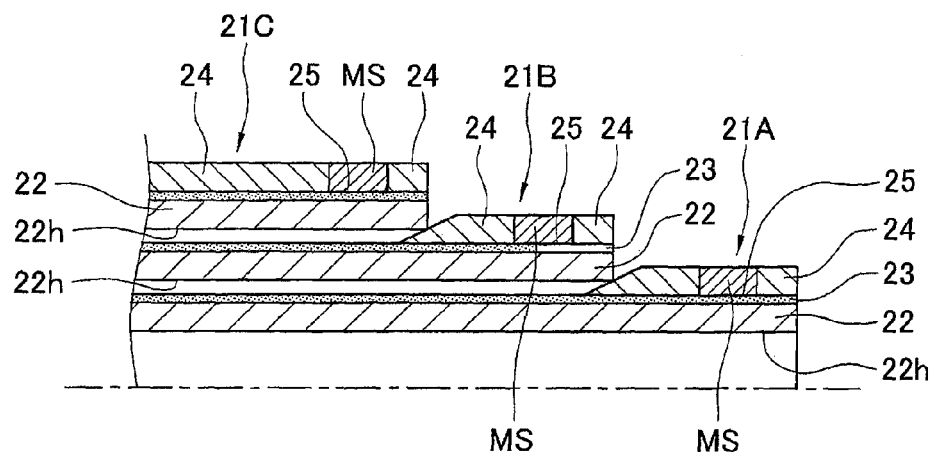
Figure 16B:
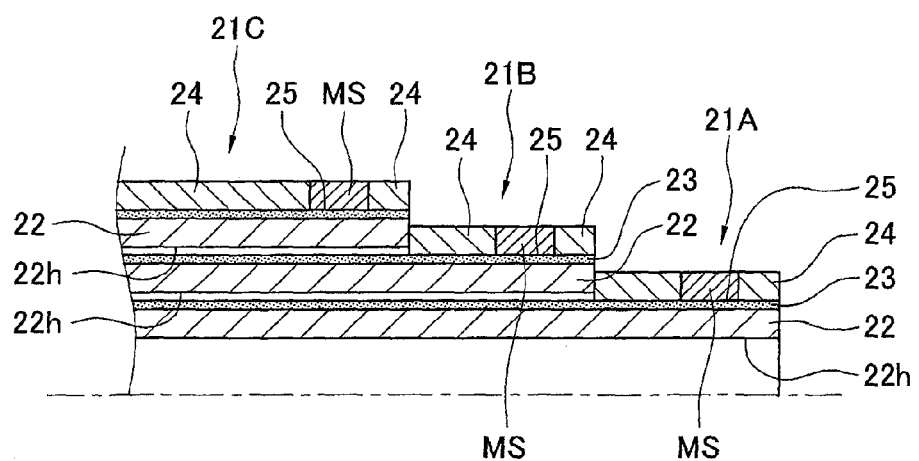

The relative positions of the tubular devices 21A-21C can be kept constant without being fixed if the insulating layers 24 at their front end parts are formed as shown in FIGS. 16A and 16B. Explained more in detail, the outer diameters of the insulating layers of the tubular devices to be inserted in (corresponding to 21A and 21B in the example of FIG. 16) are made bigger than the inner diameters of the tubular devices on the receiving side (corresponding to 21B and 21C in the example of FIG. 16) as shown in FIGS. 16A and 16B such that the length by which the tubular devices to be inserted can be inserted can be limited. In other words, the distance by which an entering tubular device protrudes from its receiving tubular device can be limited.

If there is provided a tubular device 21 without having any sensing substance MS provided to its electrode section 25, as in the example described above, the concentration and quantity of the object under test can be measured without providing a counter electrode separate from the biosensor BC. If a counter electrode is provided apart from the biosensor BC, however, it becomes possible to provide the sensing substance MS to the electrode sections 25 of all of the tubular devices 21A-21C to measure the concentration and quantity of the object under test.

Since even the thinnest of the tubular devices (21A) has a throughhole 22h formed in its axial direction therethrough, it is possible to place another sensor inside an organism through this throughhole 22h. Thus, even a relatively weak sensor that itself cannot be inserted into an organism by penetration such as a sensor having optical fibers can be inserted close to a position where the biosensor BC of this embodiment is measuring concentration, etc. and hence it becomes possible to make measurements by using the optical fibers in addition to concentration, etc. It is convenient because, for example, measurements of oxygen concentration, pH and surface pressure, use as an optical biosensor by attaching antibodies or organisms on the front surface of optical fibers as recognition elements and measurements by surface plasmon resonance may become feasible.

Since it is also possible to collect matters in the neighborhood of the front end through the throughhole 22h, cancer cells and tumors in an organism can be inspected from collected cells.

Moreover, if the tubular member 22 of the tubular device 21 is made of an insulating material, it is possible to reduce the possibility of short-circuiting between the conductive layer 23 and another sensor placed in the throughhole when a voltage is applied to the conductive layer 23 of the tubular device 21. Thus, measurements can be carried out accurately even if the sensor is a precision instruction susceptive to and easily influenced by electrical noise, etc. and generation of errors can be prevented.

The tubular members 22 of the tubular devices 21 may be made of a material usable for the conductive layer 23. In such a case, it becomes unnecessary to provide the tubular device 21 separately with a conductive layer 23, although the possibility of occurrence of short-circuiting becomes high with another sensor placed in the throughhole 22h or the conductive layer 23 of another tubular device 21. In other words, it becomes possible to form an electrode section 25 and a signal detection section 26 merely by providing only an insulating layer 24 and exposing the surface of the tubular member 22 by removing this insulating layer 24. Thus, the tubular device 21 can be made thinner by the thickness of the conductive layer 23 while maintaining the functions of tubular devices having a conductive layer and the number of production steps for tubular devices can be reduced.

The tubular member 22 of the tubular device 21 may be not only formed with a material usable for the conductive layer 23 but also provided further with conductive layer 23 on its surface. In such a case, if the conductive layer 23 is formed with a material with higher conductivity than the material for the tubular member 22, it is possible to provide higher conductivity to the tubular device 21 by way of the material of the conductive layer 23 while maintaining strength by way of the material of the tubular member 22.

Only one of the tubular devices 21 can alone be used as a biosensor. In other words, if a single tubular device 21 and a counter electrode are inserted into an organism and a voltage is applied between the signal detection section 26 of the tubular device 21 and the counter electrode, it is possible to detect the current flowing between them, etc. and hence the concentration of substances near the front end of the tubular device 21. Since another sensor can be inserted through the throughhole 22h of the tubular device 21, effects similar to those of the biosensor BC described above can be obtained.

In this case, an optimum value of the voltage to be applied between the signal detection section 26 and the counter electrode may be determined according to the kind of the sensing substance and the purpose of the measurement. In the case of a measurement of the glucose concentration by glucose oxidase, for example, if the material for the conductive layer 23 and the counter electrode is silver-silver chloride, the voltage to be applied between the two electrodes might be between about −0.5V and +1.0V.

Figure 17A:
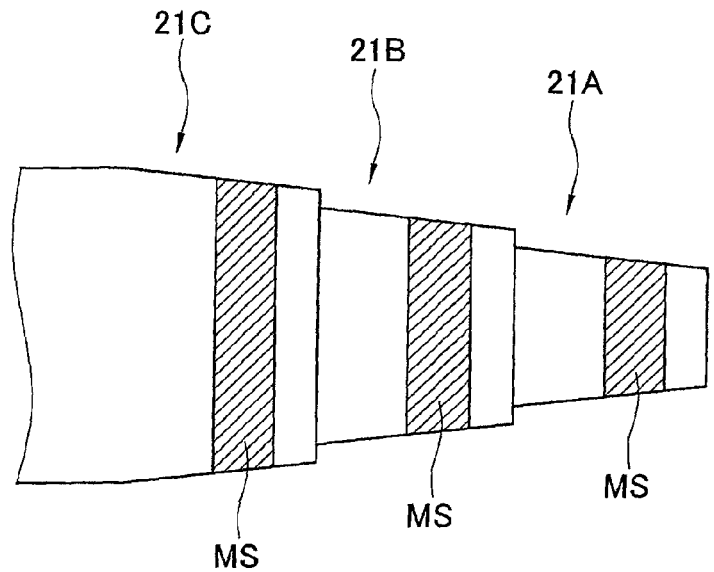
FIG. 17A is a schematic enlarged side view of the front end part of a biosensor according to still another embodiment of this invention.
Figure 17B:
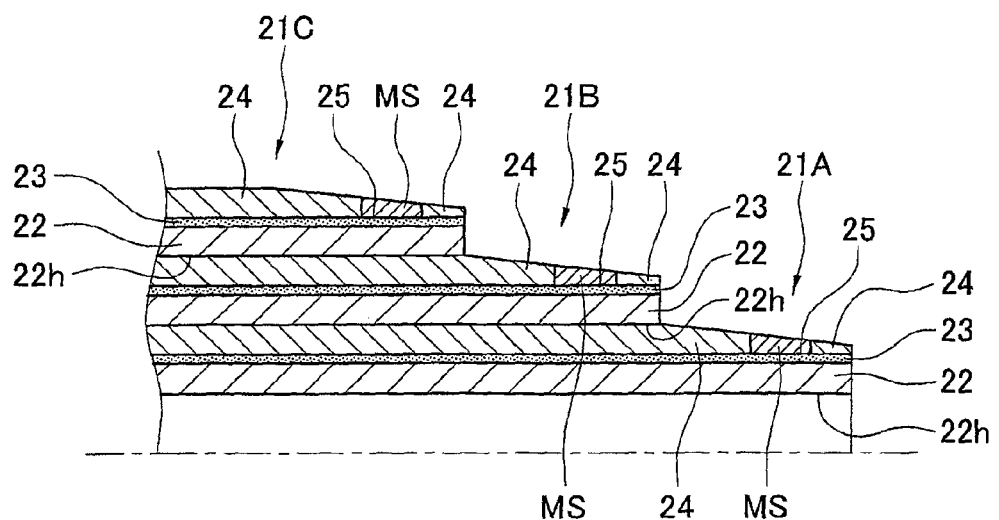
FIG. 17B is its schematic enlarged sectional view.

The biosensor BC may also be formed with the tubular devices 21A and 21B protruding further than the outer tubular devices such that their end parts become thinner towards their ends, as shown in FIG. 17. This is convenient because the resistance can be reduced when the biosensor BC is used to penetrate an organism. If the end part of the tubular device is shaped so as to become narrower towards the end or made in a shape of being cut by an inclined plane with respect to the axial direction, or in the shape of a hypodermic needle (as shown in FIG. 3B), the resistance at the time of penetration or insertion can be reduced and the burden imposed on the organism can be reduced.

Each tubular device 21 is formed such that its front end is of a truncated conical shape, but the sloping angle of the side surface of the truncated conical shape with respect to the central axis may but need not be the same for all of the tubular devices 21A-21C.

If mutually adjacent pairs of the tubular devices are fixed together by means of an insulating member 27, as shown in FIG. 15B, the possibility of current leakage between these pairs can be further reduced.

Figure 15A:
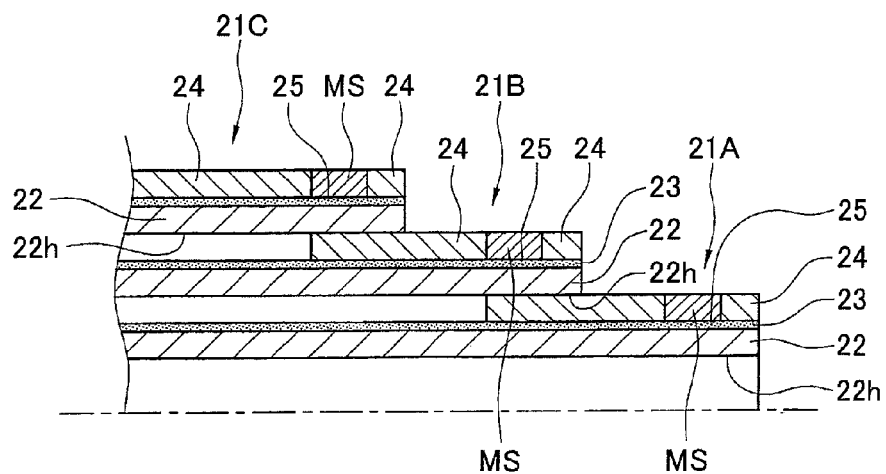
FIG. 15, consisting of FIGS. 15A and 15B, and FIG. 16, consisting of FIGS. 16A and 16B, are schematic enlarged sectional diagrams of the front end part of biosensors according to other embodiments of this invention.
Figure 15B:
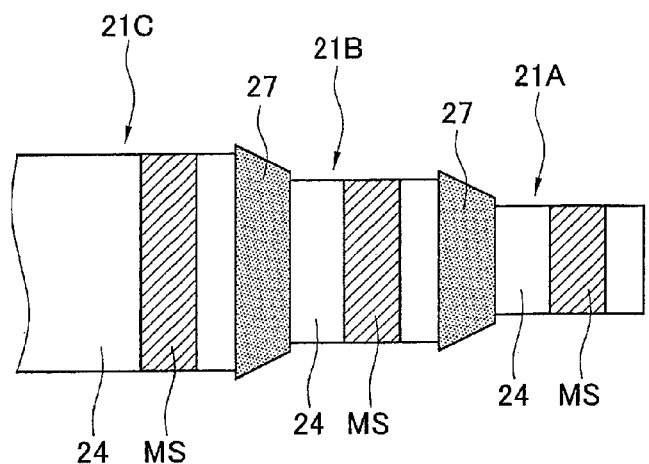

The insulating layer 24 may be formed on only a part of the conductive layer 23 as shown in FIGS. 15A and 16. This is convenient for improving workability for assembling when the linear characteristics of the tubular devices 21 is not good because many gaps can be maintained when they are assembled in a nesting form. It is also effective for improving workability for assembling when graphite is used as the material for the conductive layers 23. When the insulating layer 24 is formed only on a part of the conductive layer 23, there may arise the problem of short-circuiting between neighboring tubular devices but since the tubular members 22 of the tubular devices 21 are made of an insulating material, this problem of short-circuiting can be reduced. It goes without saying, however, that it is more effective to reduce the possibility of short-circuiting by forming the insulating layer 24 to cover the conductive layer 23 entirely.

Next, the structure of tubular devices 21 forming the biosensor BC is explained.

In FIGS. 13 and 14, numeral 21 generally indicates a tubular device forming a biosensor BC. The tubular device 21 is a linear member elongated in its axial direction (in the left-right direction in FIG. 14). Although FIGS. 13 and 14 show an example where the sectional shape of the tubular device 21 is circular, the sectional shape is not limited to be circular. It may be semi-circular or polygonal such as a square, a rectangle or a polygon such as a hexagon or an octagon.

The tubular device 21 is provided with a tubular member 22 which is a hollow tubular member extending in its axial direction and provided with a throughhole 22h passing therethrough axially from its base end to the front end. This throughhole 22h serves as the throughhole through the tubular device 21. The sectional shape of the tubular member 22 is not limited to be circular. It may be semi-circular or polygonal such as a square, a rectangle or a polygon such as a hexagon or an octagon.

Although FIG. 14 shows that the sectional shapes of the tubular device 21 and the tubular member 22 are similar, furthermore, they need not be similar. For example, the sectional shape of the tubular device 21 may be circular while that of the tubular member 22 is semicircular or polygonal, and the sectional shape of the tubular device 21 may be semicircular or polygonal while that of the tubular member 22 is circular.

The throughhole 22h is only required to be approximately tubular, and its sectional shape is not limited to be circular. It may be semi-circular or polygonal such as a square, a rectangle or a polygon such as a hexagon or an octagon.

Although FIG. 14 shows that the sectional shapes of the tubular member 22 and the throughhole 22h are similar, furthermore, they need not be similar. For example, the sectional shape of the tubular member 22 may be circular while that of the throughhole 22h is semicircular or polygonal, and the sectional shape of the tubular member 22 may be semicircular or polygonal while that of the throughhole 22h is circular.

The tubular device 21 need not be provided with the tubular member 22 and may be formed only with the conductive layer 23 and the insulating layer 24 so as to have the throughhole. If the tubular member 22 is provided, however, the strength of the tubular device 21 can be improved because the tubular member 22 can be made to function as the shaft of the tubular device 21.

A layer made of a conductive material (conductive layer 23) and another layer made of an insulating material (insulating layer 24) are alternately provided to the side surface of the tubular member 22 along a direction transverse to the axial direction of the tubular member 22, as shown in FIGS. 13 and 14.

Although FIGS. 13 and 14 show an example wherein there is one conductive layer and one insulating layer, pluralities of conductive and insulating layers may be provided as long as they are formed alternately.

Although FIG. 13 shows an example wherein a conductive layer 23 is formed on the side surface of the tubular member 22, it goes without saying that it may be an insulating layer 24 that is formed on the side surface of the tubular member 22, a conductive layer 23 being formed on its surface and another insulating layer 24 being formed on the surface of this conductive layer 23.

FIGS. 13 and 14 show that an electrode section 25 is formed on an end part (on the right-hand end in FIG. 13) of the tubular device 21 by removing the insulating layer 24 to expose the surface of the conducive layer 23.

Although the electrode section 25 is formed from a part of the conductive layer 23 in FIGS. 13 and 14, the electrode section 25 may be formed with another conductive material apart from the conductive layer 23. In this case, the electrode section 25 may be formed by a conductive member on the surface of the insulating layer 24 apart from the conductive layer 23, this electrode section 25 being electrically connected with the conductive layer 23.

As shown in FIG. 14, a signal detection section 26 is formed with a conductive material on a base end side (on the left-hand end in FIG. 14) of the tubular device 21. This signal detection section 26 is connected to a power source DC, an ammeter A, a volt meter V, etc. As a result, a voltage can be applied to the electrode section 25 through the conductive layer 23 by applying a voltage to the signal detection section 26.

A portion of the insulating layer 24 may be removed to expose the conductive layer 23 so as to make the exposed portion usable as the signal detection section 26.

Although the conductive layer 23 is intended to function as the lead line for electrically connecting the signal detection section 26 with the electrode section 25, the conductive layer 23 need not be provided if a lead line such as an electric wire is provided to the tubular device 21 so as to connect them electrically together. If the conductive layer 23 is made to function as a lead line, however, it becomes easier to make the tubular devices 21 thinner and there are advantages such that a portion of the conductive layer 23 can be used as the electrode section 25 or the signal detection section 26, as explained above.

Next, the materials for the individual components of the tubular devices 21 are explained.

The tubular members are formed with insulating materials such as super-elastic resin, PET, polyphenylene diamine, polyurethane, nylon, vinyl polychloride, polysiloxane, glass ($SiO_2$), polypropylene, polythiophene, polyester, polyethylene, urea resins, polysilane. polyaniline, metal oxides and alloys, but there is no particular limitation.

If super-elastic resin is used, in particular, the tubular device 21 and the biosensor BC can be prevented more reliably from bending or becoming damaged when they are penetrated into the object under test while they are being rotated around the central axis because the elasticity of super-elastic resins is particularly high such that the tubular device 21 and the biosensor BC can be more reliably inserted into the object under test such as organisms. Preferable examples of super-elastic resin include polyisoprene, styrene-butadien copolymers, polyethylene, fluorine resins, polyethylene+nylon, polyethylene+perprene, esters of polyacrylic acid, esters of polymethacrylic acid, polysiloxane, silicon resins, vinyl polychloride, polyethylene chloride, perprene, polyethylene+vinyl polychloride, polyethylene+fluorine resin, polyurethane, polyimide, polyamide and polysilane. In particular, fluorine resins and polysiloxane, which are not easily rejected by organisms, having fitness to organisms, are preferred.

The conductive layer 23 is formed with a conductive material on the outer peripheral surface of the tubular member 22 by a thin-film method such as vapor deposition, sputtering and electroless plating, although the method of forming the conductive layer 23 is not limited to these methods and any method may be used for the purpose.

Examples of the material that may be used for the conductive layer 23 include super-elastic alloys, gold, silver, copper, platinum, alloys such as platinum-iridium alloy, palladium, nickel, titanium, carbon, polypyrol, polythiophene, polyaniline and polyacetylene, but there is no particular limitation.

If use is made of a super-elastic alloy as the material for the conductive layer 23, in particular, since the elasticity of super-elastic alloys is very high, not only the tubular member 22 but also the conductive layer 23 can support the force applied to the biosensor BC and hence the tubular device 21 and the biosensor BC can be prevented more reliably from bending or becoming damaged when they are penetrated into the object under test while they are being rotated around the central axis, such that the tubular device 21 and the biosensor BC can be more reliably inserted into the object of test such as organisms. Preferable examples of super-elastic alloy include titanium-nickel alloys (Ti—Ni), indium-thallium alloys (In—Tl), copper-zinc alloys (Cu—Zn), copper-zinc-X alloys (Cu—Zn—X(Si, Sn, Al, Ga)), copper-aluminum-nickel alloys (Cu—Al—Ni), copper-gold-zinc alloys (Cu—Au—Zn), copper-tin alloys (Cu—Sn), nickel-aluminum alloys (Ni—Al), iron-platinum alloys (Fe—Pt), indium-cadmium alloys (In—Cd), manganese-copper alloys (Mn—Cu), silver-cadmium alloys (Ag—Cd), gold-cadmium alloys (Au—Cd), iron-palladium alloys (Fe—Pd), iron-nickel-cobalt-titanium alloys (Fe—Ni—Co—Ti), iron-nickel-carbon alloys (Fe—Ni—C), iron-manganese-silicon alloys (Fe—Mn—Si), titanium-aluminum-tin-zirconium-molybdenum alloys (Ti—Al—Sn—Zr—Mo), titanium-aluminum-vanadium alloys (Ti—Al—V), titanium-molybdenum-aluminum alloys (Ti—Mo—Al), titanium-niobium alloys (Ti—Nb), titanium-niobium-tin alloys (Ti—Nb—Sn), and titanium-vanadium-iron-aluminum alloys (Ti—V—Fe—Al). In particular, alloys not containing copper, nickel and cadmium which are harmful to organisms are preferred.

When platinum is used as material for the conductive layer 23, if the conductive layer 23 of platinum are formed after a layer of a different material is formed as substrate prior to the formation of the platinum layer, it is possible to improve the adhesive characteristic of platinum.

The insulating layer 24 is formed on the surfaces of the conductive layer 23 by a thin film method such as the vapor deposition method and the sputtering method but their formation is not limited to these methods, and any suitable method may be used for the purpose.

The insulating layer 24 is formed by using a material with an insulating characteristic that is equivalent to that of the tubular member 22 such as super-elastic resins, PET, polyphenylene diamine, polyurethane, nylon, vinyl polychloride, polysiloxane, glass ($SiO_2$), polypropylene, polythiophene. polyester, polyethylene, urea resins, polysilane, polyaniline and metal oxides, but there is no particular limitation.

Next, an example of the production method of the tubular device 21 is explained.

Figure 18A:
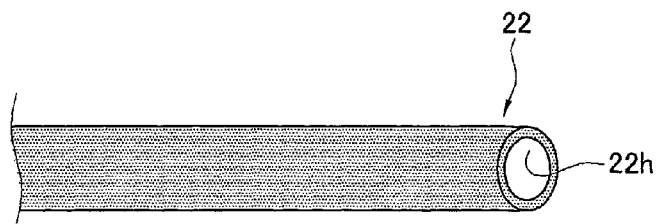
FIG. 18, consisting of FIGS. 18A, 18B, 18C, 18D and 18E, shows production steps of a tubular device according to this invention.
Figure 18B:
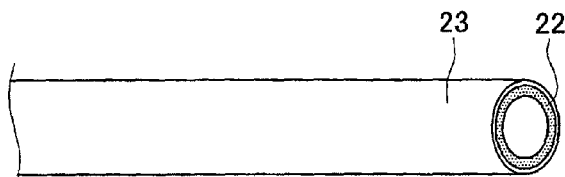
Figure 18C:
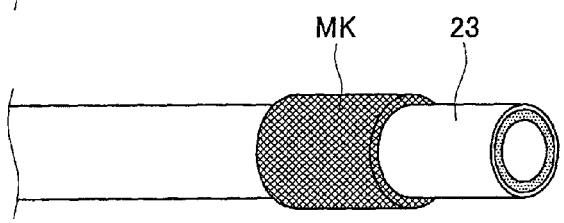

The tubular device 21 as described above is produced firstly by forming the conductive layer 23 on the outer peripheral surface of the tubular member 22 by attaching a conductive material by a method such as sputtering, as shown in FIGS. 18A and 18B, and then forming a mask MK on the surface of the conductive layer 23, as shown in FIG. 18C.

Figure 18D:
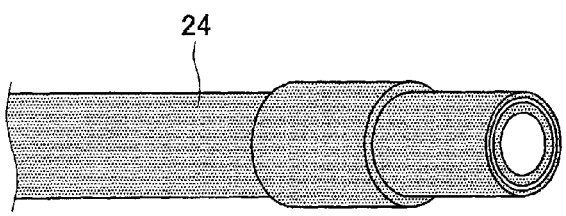
Figure 18E:
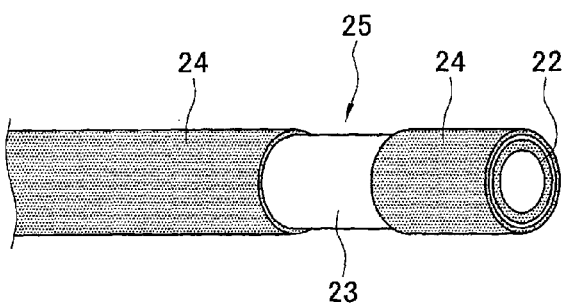

Next, the insulating layer 24 is formed as shown in FIG. 18D by attaching by a method such as sputtering an insulating material on the outer peripheral surface where the conductive layer 23 and the mask MK have been formed, the mask MK being thereafter removed as shown in FIG. 18E. As a result, the electrode section 25 and the signal detection section 26 are formed where the mask MK has been removed to expose the conductive layer 23 and the tubular device 21 according to the present embodiment is obtained.

The biosensor BD is obtained if the sensing substances MS are placed at the electrode sections 25 of these tubular devices 21 and these tubular devices 21 are combined together. Since the tubular devices 21 are formed separately and then combined together, the formation of the biosensor BC becomes simpler and the placing of the sensing substances MS at the electrode sections also becomes reliable.

In order to ascertain the capability of the biosensor of this invention using a rod-shaped device, the concentration of glucose was varied to examine the changes in the response current flowing through the sensor.

In this experiment, a biosensor of this invention and an Ag/AgCl electrode serving both as the counter electrode and the reference electrode were immersed in a buffer solution (0.1 M) of phosphoric acid with pH 7.4 and the glucose concentration in the buffer solution was measured by applying a voltage of 0.6V to obtain the relationship between the glucose concentration and the response current. The batch amperometry method was used for the measurement of the response current, as shown in FIG. 6.

The biosensor that was used for the experiment comprised a platinum tube with its outer peripheral surface coated with silica, having outer diameter of 0.5 mm and inner diameter of 0.3 mm, having enzyme (glucose oxidase) affixed as explained below on the inner surface of the tube, as shown in FIG. 4A. The electrode area of this biosensor, or the area of the inner surface of the platinum tube where enzyme was attached was 0.35 $mm^2$. It was four days after the sensor was produced that it was used for this experiment.

Enzyme was attached to the inner surface of the platinum tube by immersing this platinum in a buffer solution (0.05M) of phosphoric acid with pH 7.0 containing deaired Tritone X-100 (0.8 mM) and glucose oxidase (10 mg/mL), applying a voltage of 1.3V (vs Ag/AgCl) for one hour, thereafter shifting the platinum tube into a buffer solution (0.05M) of phosphoric acid with pH 7.4 containing 1,2-phenylene diamine (5.40 mg/mL) and applying a voltage of 0.7V (vs Ag/AgCl) for 15 minutes.

Figure 19:
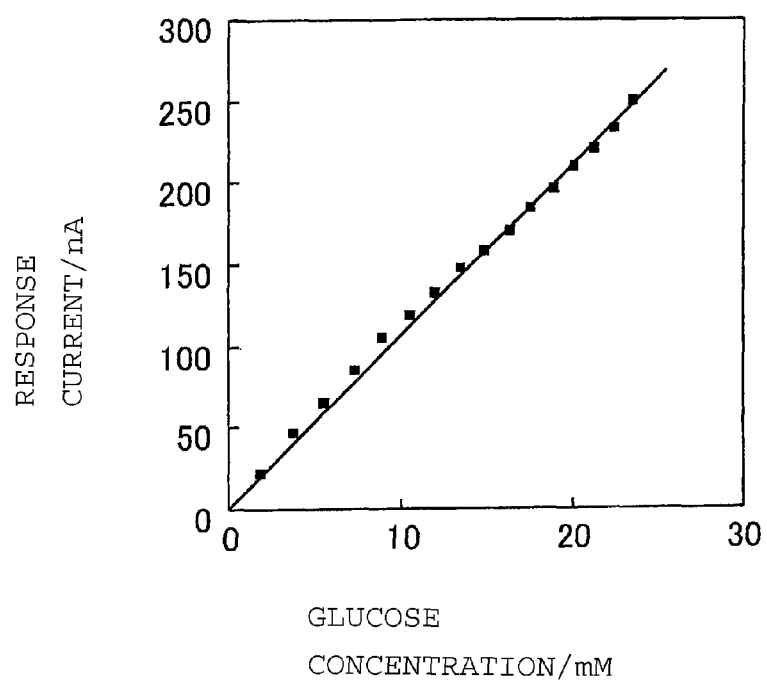
FIG. 19 is a graph showing the relationship between glucose concentration and response current for a biodevice using a rod-shaped device of this invention.

As shown in FIG. 19, a good linear relationship passing through zero has been obtained between glucose concentration and sensor response current in the range of 0-25 mM (0-about 450 mg/dL). This indicates that the range in which concentration can be measured accurately by the biosensor of this invention is quite wide and that an accurate measurement of concentration is possible even if the object under test has a very high concentration.

Biosensors according to this invention are suited for multi-purpose medical instruments for simultaneously measuring a concentration inside an organism and the hearth condition of that organism.

What is clamed is:

1. A biodevice formed in an elongated form that is inserted inside an organism and capable of directly detecting and measuring an object under test inside the organism comprising:
   a shaft member at a center position of said biodevice, said shaft member extending in an axial direction and having a shaft diameter of 500 μm or less; and
   a conductive layer and an insulating layer which are stacked on a side surface of said shaft member in a direction transverse to said axial direction;
   wherein said biodevice has a cylindrical hollow section formed therethrough, being connected to the exterior at a front end and extending from said front end in said axial direction, said hollow section having an electrode section on an inner surface; and
   wherein said hollow section is formed such that a front end of said shaft member is disposed at an inner bottom part of said hollow section said hollow section containing a member that varies volume or affinity by an external optical, thermal, or electrical stimulus.

2. The biodevice of claim 1 wherein said electrode section is formed along said inner surface of said hollow section so as to have an approximately cylindrical surface.

3. The biodevice of claim 2 wherein said electrode section is formed by a part of said conductive layer.

4. The biodevice of claim 2 wherein said hollow section contains a member that varies volume or affinity by an external optical, thermal or electrical stimulus.

5. The biodevice of claim 1 adapted for use with a front end part disposed inside an organism, said shaft diameter becoming smaller towards the front end part.

6. A contact part structure of a biodevice which is a structure of a contact part of a device adapted to be placed in an organism and capable of directly detecting and measuring an object under test inside the organism, a base of said device being connected to a base end, said contact part being adapted to contact said organism and having a shaft diameter of 500 μm or less;
   wherein said contact part structure comprises a shaft member at a center position of said contact part, said shaft member extending in an axial direction, and a conductive layer and an insulating layer which are stacked on a side surface of said shaft member in a direction transverse to said axial direction; and
   wherein said contact part structure has a cylindrical hollow section formed therethrough, being connected to the exterior at a front end and extending from said front end in said axial direction, said hollow section having an electrode section on an inner surface; and
   wherein said hollow section is formed such that a front end of said shaft member is disposed at an inner bottom part of said hollow section, said hollow section containing a member that varies volume or affinity by an external optical, thermal, or electrical stimulus.

7. The contact part structure of claim 6 wherein said electrode section is formed along said inner surface of said hollow section so as to have an approximately cylindrical surface.

8. The contact part structure of claim 7 wherein said electrode section is formed by a part of said conductive layer.

9. The contact part structure of claim 7 wherein said hollow section contains a member that varies volume or affinity by an external optical, thermal or electrical stimulus.

10. The contact part structure of claim 6 adapted for use with a front end part disposed inside an organism, said shaft diameter becoming smaller towards the front end part.

* * * * *